Figure 1A:
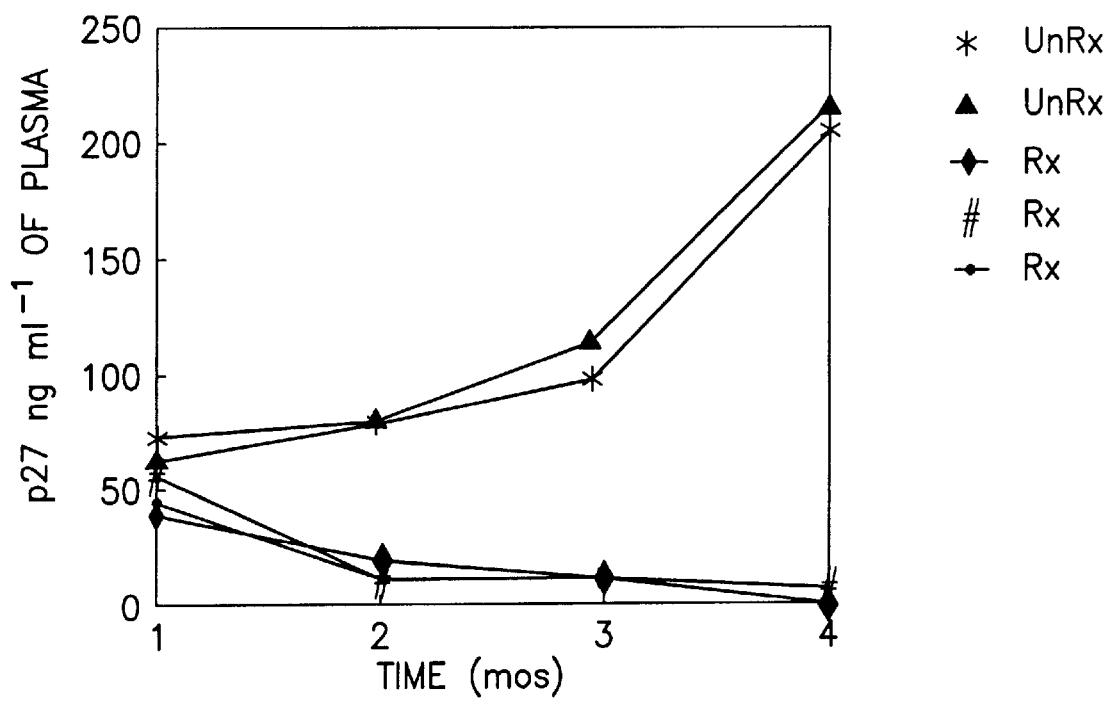
Figure 1B:
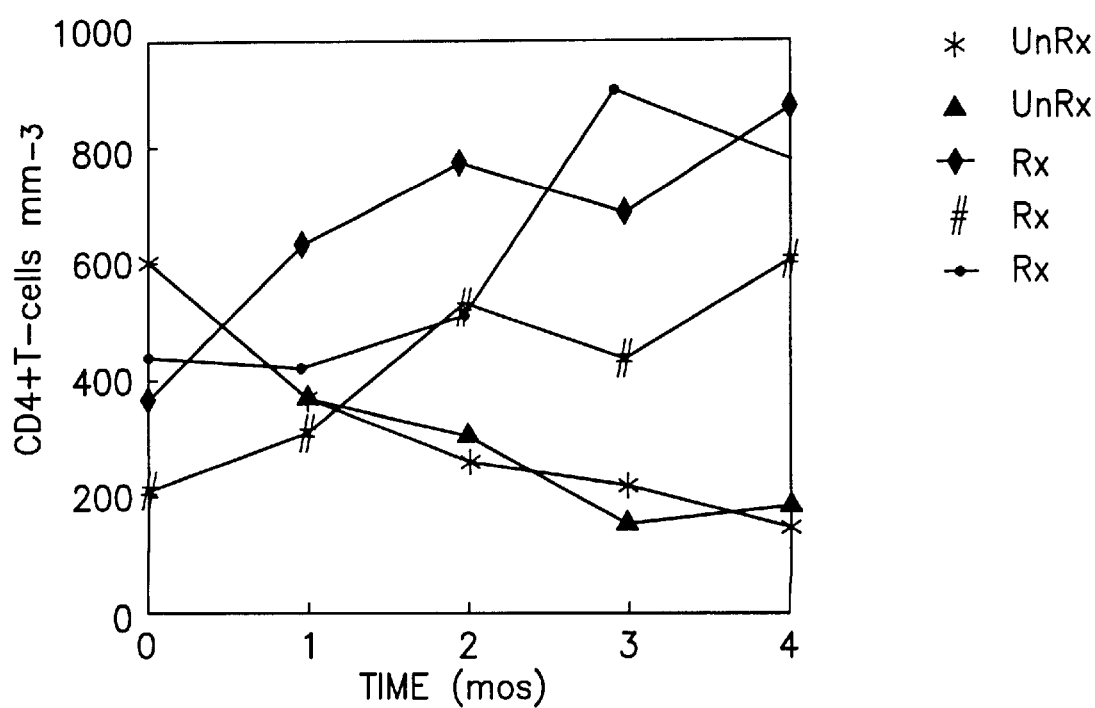
Figure 1C:
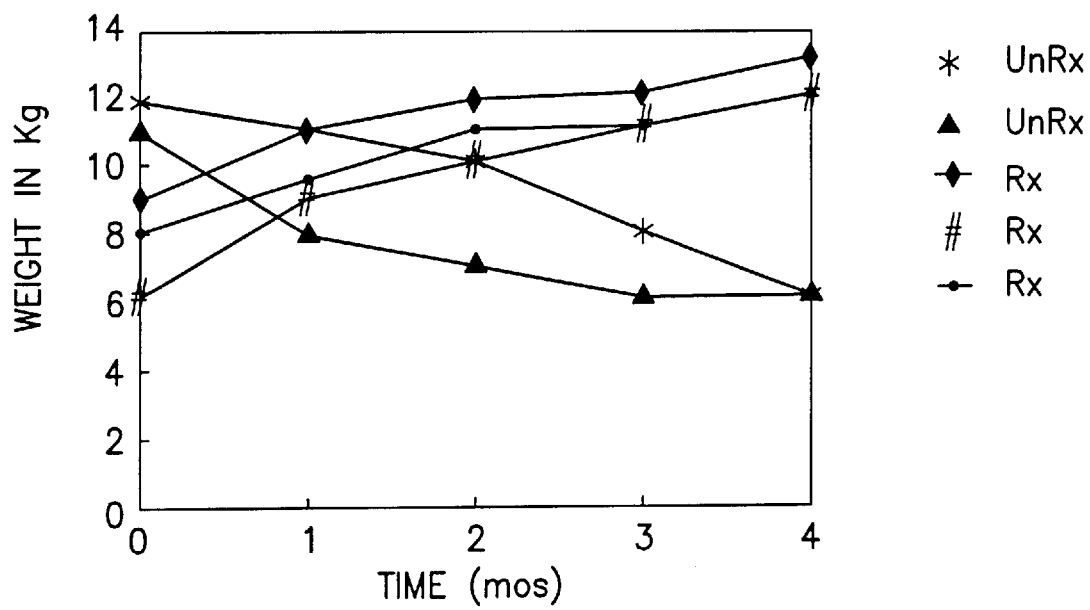

United States Patent [19]
Gallo et al.

[11] Patent Number: 5,968,513
[45] Date of Patent: *Oct. 19, 1999

[54] METHOD OF PROMOTING HEMATOPOIESIS USING DERIVATIVES OF HUMAN CHORIONIC GONADOTROPIN

[75] Inventors: Robert C. Gallo, Bethesda; Joseph Bryant, Rockville; Yanto Lunardi-Iskandar, Gaithersburg, all of Md.

[73] Assignee: University of Maryland Biotechnology Institute, College Park, Md.

[ * ] Notice: This patent is subject to a terminal disclaimer.

[21] Appl. No.: 08/709,924

[22] Filed: Sep. 9, 1996

Related U.S. Application Data

[63] Continuation-in-part of application No. 08/669,654, Jun. 24, 1996, abandoned.

[51] Int. Cl.$^6$ .............................. A61K 38/12; C07K 7/64
[52] U.S. Cl. ................................... 424/185.1; 424/198.1; 514/2; 514/14; 514/15; 514/16; 514/17; 514/18; 514/885; 530/320; 530/321; 530/322; 530/323; 530/324; 530/325; 530/326; 530/327; 530/328; 530/329; 530/330
[58] Field of Search ................................. 514/2.14–181, 514/885; 424/185.1, 198.1; 530/320–330

[56] References Cited

U.S. PATENT DOCUMENTS

| | | | |
|---|---|---|---|
| 4,400,316 | 8/1983 | Katsuragi et al. | 260/112.5 |
| 4,689,222 | 8/1987 | McMichael | 424/88 |
| 4,691,006 | 9/1987 | Stevens | 530/324 |
| 4,692,332 | 9/1987 | McMichael | 424/88 |
| 4,713,366 | 12/1987 | Stevens | 514/13 |
| 4,714,680 | 12/1987 | Civin et al. | 435/240.25 |
| 4,880,626 | 11/1989 | McMichael | 424/88 |
| 4,966,753 | 10/1990 | McMichael | 424/88 |
| 5,004,681 | 4/1991 | Boyse et al. | 435/2 |
| 5,192,553 | 3/1993 | Boyse et al. | 424/529 |
| 5,380,668 | 1/1995 | Herron | 436/510 |
| 5,451,527 | 9/1995 | Sarin et al. | 436/518 |
| 5,494,899 | 2/1996 | Kincade et al. | 514/21 |
| 5,700,781 | 12/1997 | Harris | 514/21 |
| 5,811,390 | 9/1998 | Bourinbaiar | 514/8 |

FOREIGN PATENT DOCUMENTS

| | | |
|---|---|---|
| 0 049 898 B2 | 4/1982 | European Pat. Off. . |
| 0 142 387 A1 | 5/1985 | European Pat. Off. . |
| WO 90/02759 | 3/1990 | WIPO . |
| WO 94/20859 | 9/1994 | WIPO . |
| WO 94/24148 | 10/1994 | WIPO . |
| WO 95/12299 | 5/1995 | WIPO . |
| WO 96/04008 | 2/1996 | WIPO . |

OTHER PUBLICATIONS

Caplus An 1991:183710 to Byull. Eksp. Biol. Med. 111(2), pp. 181–183, Feb. 1991.
Caplus An 1990:132643 to Byull. Eksp. Biol. Med. 109(1), pp. 62–64, Jan. 1990.
1996 Sigma Product Catalogue, p. 1134.
Abrams et al., 1983, J. Cell. Biochem. Suppl. 7A:53.
Aizawa and Tavassoli, 1986, Int. J. Cell Cloning 4:464–471.
Andrews et al., 1986, Blood 67:842–845.
Andrews et al., 1986, Blood 68:1030–1035.
Ballem et al., 1987, J. Clin. Invest. 80:33–40.
Ballem et al., 1992, New Eng. J. Med. 327:1779–1784.
Barre–Sinoussi et al., 1983 Science 220:868–870.
Bauman et al., 1986, J. Cell. Physiol. 128:133–142.
Bellet et al., 1984, Endocrinology 115:330–336.
Berchtold and Wenger, 1993, Blood 81:1246–1250.
Bidart et al., 1987, Mol. Immunology 24:339–345.
Bidart et al., 1987, J. Biol. Chem. 262:15483–15489.
Bidart et al., 1990, Science 248:736–739.
Bodger et al., 1983, Blood 61:1006–1010.
Braunstein et al., 1978, J. Clin. Endocrinology and Metabolism 47:326–332.
Broxmeyer et al., 1984, J. Clin. Invest. 73:939–953.
Broxmeyer, 1983, CRC Critical Reviews in Oncology/Hematology 1:227–257.
Broxmeyer, 1982, J. Clin. Invest. 69:632–642.
Busch et al., 1987, Blut 54:179–188.
Cain et al., 1986, Transplantation 41:22–25.
Cao et al., 1982, J. Med. Genet. 19:81–87.
Caraux et al., 1985, J. Immun. 134:835–840.
Daffos et al., 1985, Am. J. Obstet. Gynecol. 153:655–660.
Daffos et al., 1983, Am. J. Obstst. Gynecol. 146:985–987.
Deshmukh et al., 1994, J. Clin. Immunol. 14:162–168.
Dexter et al., 1977, J. Cell. Physiol. 91:335–344.
Dirnhofer et al., 1994, J. Endocrinology 141:153–162.
Dirnhofer et al., 1993, FASEB J. 7:1381–1385.
Emerson et al., 1985, J. Clin. Invest. 76:1286–1290.
Ferrero et al., 1986, Cancer Res. 46:975–980.
Ferrero et al., 1983, Proc. Natl. Acad. Sci. USA 80:4114.
Geller et al., 1985, Archs. Path. Lab. Met 109:138–145.
Gill et al., 1996, New Eng. J. Med. 335:1261–1269.
Goldman et al., 1980, Br. J. Haematol. 45:223–221.
Harris, 1995, Lancet 346:118–119.

(List continued on next page.)

*Primary Examiner*—Bennett Celsa
*Attorney, Agent, or Firm*—William A. Barrett; Steven J. Hultquist

[57] ABSTRACT

The present invention relates to methods of treating or preventing diseases or disorders associated with hematopoietic deficiency by administration of human chorionic gonadotropin, β-human chorionic gonadotropin or a peptide containing a sequence of a portion of β-human chorionic gonadotropin. The invention also relates to methods of treating or preventing diseases or disorders associated with hematopoietic deficiency by administration of hematopoietic cells, the numbers of which have been increased by contacting the cells with human chorionic gonadotropin, β-human chorionic gonadotropin or a peptide containing a sequence of a portion of β-human chorionic gonadotropin. The invention also provides assays for the utility of particular human chorionic gonadotropin preparations in the treatment or prevention of hematopoietic deficiencies or in the increasing of hematopoietic cell numbers in vitro. Pharmaceutical compositions and methods of administration of are also provided.

104 Claims, 10 Drawing Sheets

OTHER PUBLICATIONS

Hermans, 1995, AIDS Res. Hum. Retroviruses S:96.
Hermans et al., 1995, Cell. Mol. Biol. 3:357–364.
Hershko et al., 1979, Lancet 1:945–947.
Hirokawa et al., 1982, Clin. Immunol. Immunopathol. 22:297–304.
Huang and Terstappen, 1992, Nature 360:745–749.
Iyer et al., 1992, Int. J. Pepetide Protein Res. 39:137–144.
Juttner et al., 1985, Br. J. Haematol. 61:739–745.
Katz et al., 1985, Leukemia Res. 9:191–198.
Katz et al., 1986, Leukemia Res. 10:961–971.
Keating et al., 1984, Blood 64:1159–1162.
Kestler et al., 1990, Science 248:1109–1112.
Keutmann et al., 1988, Biochemistry 27: 8939–8944.
Keutmann et al., 1987, Proc. Natl. Acad. Sci. USA 84: 2038–2042.
Kodo et al., 1984, J. Clin. Invest. 73:1377–1384.
Korbling et al., 1986, Blood 67:529–532.
Kornyei et al., 1993, Biol. Reprod. 49:1149–1157.
Lajtha, 1979, Diferentiation 14:23–24.
Lajtha, 1979, Blood Cells 5:447–455.
Lapthron et al., 1994, Nature 369:455–461.
Leary et al., 1987, Blood 69:953–956.
Letvin et al., 1990, J. AIDS 3:1023–1040.
Longhi et al., 1986, J. Immunol. Meth. 92:89–95.
Lord and Spooncer, 1986, Lymphokine Res. 5:59–72.
Louache et al., 1992, Blood 180:2991–2999.
Lu et al., 1983, Blood 61:250–256.
Lunardi–Iskandar et al., 1995, Nature 375:64–68.
Lunardi–Iskandar et al., 1989, J. Clin. Invest. 83:610–615.
Lunardi–Iskandar et al., 1989, Leukemia Res. 13:573–581.
Moore et al., 1980, Blood 55:682–690.
Nicola et al., 1980, J. Cell. Physiol. 103:217–237.
Nicola et al., 1981, Blood 58:376–386.
Nijhof et al., 1984, Exp. Cell. Res. 155:583–587.
Nijhof et al., 1983, J. Cell. Biol. 96:386–392.
Nothdurtt et al., 1977, Scand. J. Haematol. 19:470–481.
Ochs et al., 1981, Pediatr. Res. 15:601.
Paige et al., 1981, J. Exp. Med. 153:154–165.
Pillow et al., 1966, New Eng. J. Med. 275:94–97.
Prummer et al., 1985, Exp. Hematol. 13:891–898.
Puisieux et al., 1990, Endocrinology 126: 687–694.
Raghavacher et al., 1983, J. Cell. Biochem. Suppl. 7A:78.
Reiffers et al., 1986, Exp. Hematol. 14:312–315.
Reisner et al., 1982, Blood 59:360–363.
Reisner et al., 1978, Proc. Natl. Acad. Sci. USA 75:2933–2936.
Robak et al., 1985, Leukemia Res. 9:1023–1029.
Rodeck, 1984, *Prenatal Diagnosis* (Royal College of Obstetricians and Gynaecologists, London).
Ryan et al., 1988, FASEB J. 2: 2661–2669.
Sarpel et al., 1979, Exp. Hematol. 7:113–120.
Smith and Broxmeyer, 1986, Br. J. Haematol. 63:29–34.
Stevens et al., 1986, Immunol. Lett. 12:11–18.
Strauss et al., 1986, Exp. Hematol. 14:935–945.
Strauss et al., 1986, Exp. Hematol. 14:878–886.
Terstappen et al., 1992, Leukemia 6:993–1000.
Thomas et al., 1972, Lancet 1(745):284–289.
Tilly et al., 1986, Lancet, Jul. 19 pp. 154–155.
To and Juttner, 1987, Br. J. Haematol. 66:285–288.
Torres et al., 1987, Immunol. Inv. 16:607–618.
Touraine, 1983, Birth Defects 19:139–142.
Tulunay et al., 1975, Proc. Natl. Acad. Sci USA 72:4 100–4104.
Valenti, 1973, Am. J. Obstet. Gynecol. 115:851–853.
Vaslin et al., 1994, AIDS Res. Hum. Retroviruses 10:1241–1250.
Vickery et al., 1983, J. Parasitol. 69:478–485.
Visser et al., 1984, J. Exp. Med. 59:1576–1590.
Ward et al., 1991, *Reproduction in Domestic Animals* (Academic Press, New York) pp. 25–80.
Weinroth et al., 1995, Infectious Agents and Disease 4:76–94.
Williams et al., 1987, Exp. Hematol. 15:243–250.
Winchester et al., 1977, Proc. Natl. Acad. Sci. USA 74:4012–4016.
Whitlock and Witte, 1982, Proc. Natl. Acad. Sci. USA 79:3608–3612.
Xia, 1993, J. Mol. Endocrinol., Jun. 10:337–343.
De, 1997, J. Clin. Invest. 99:1484–1491.

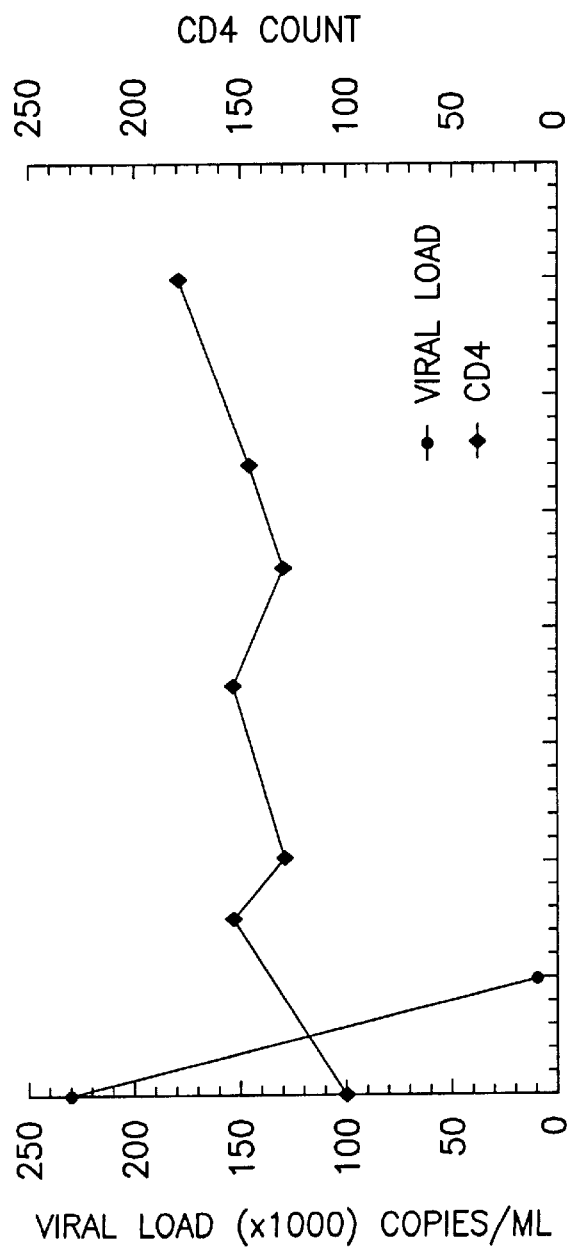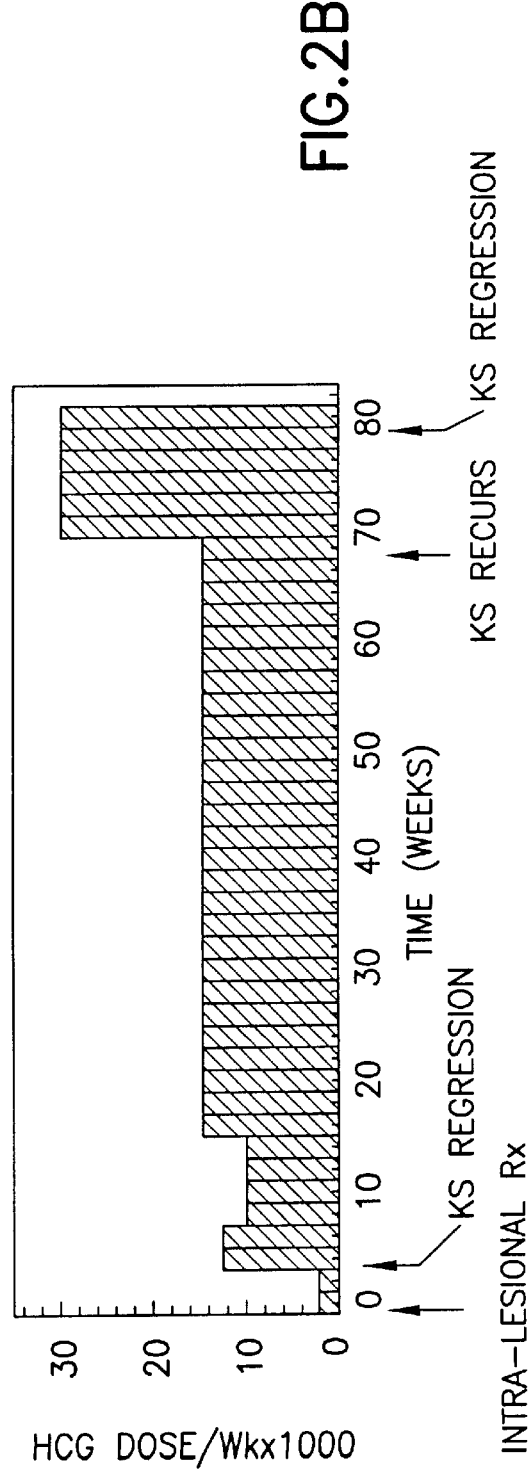

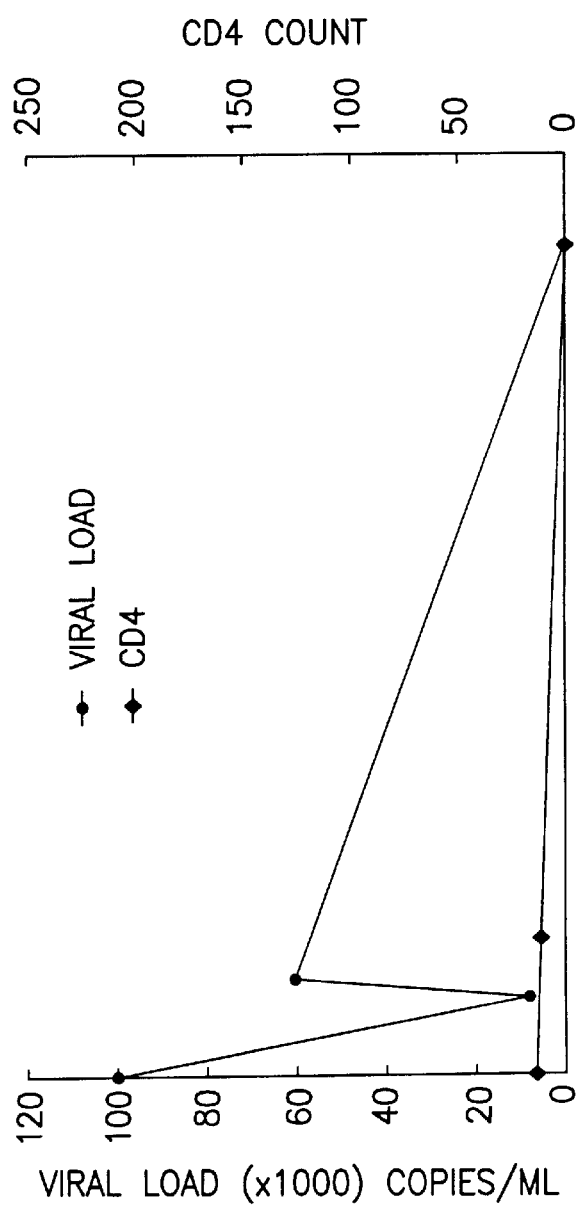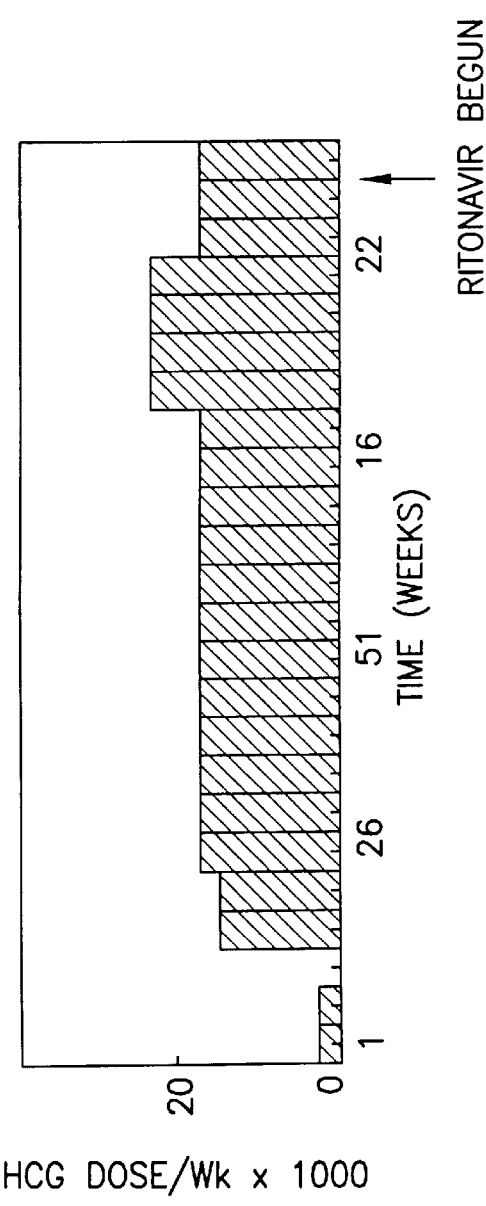

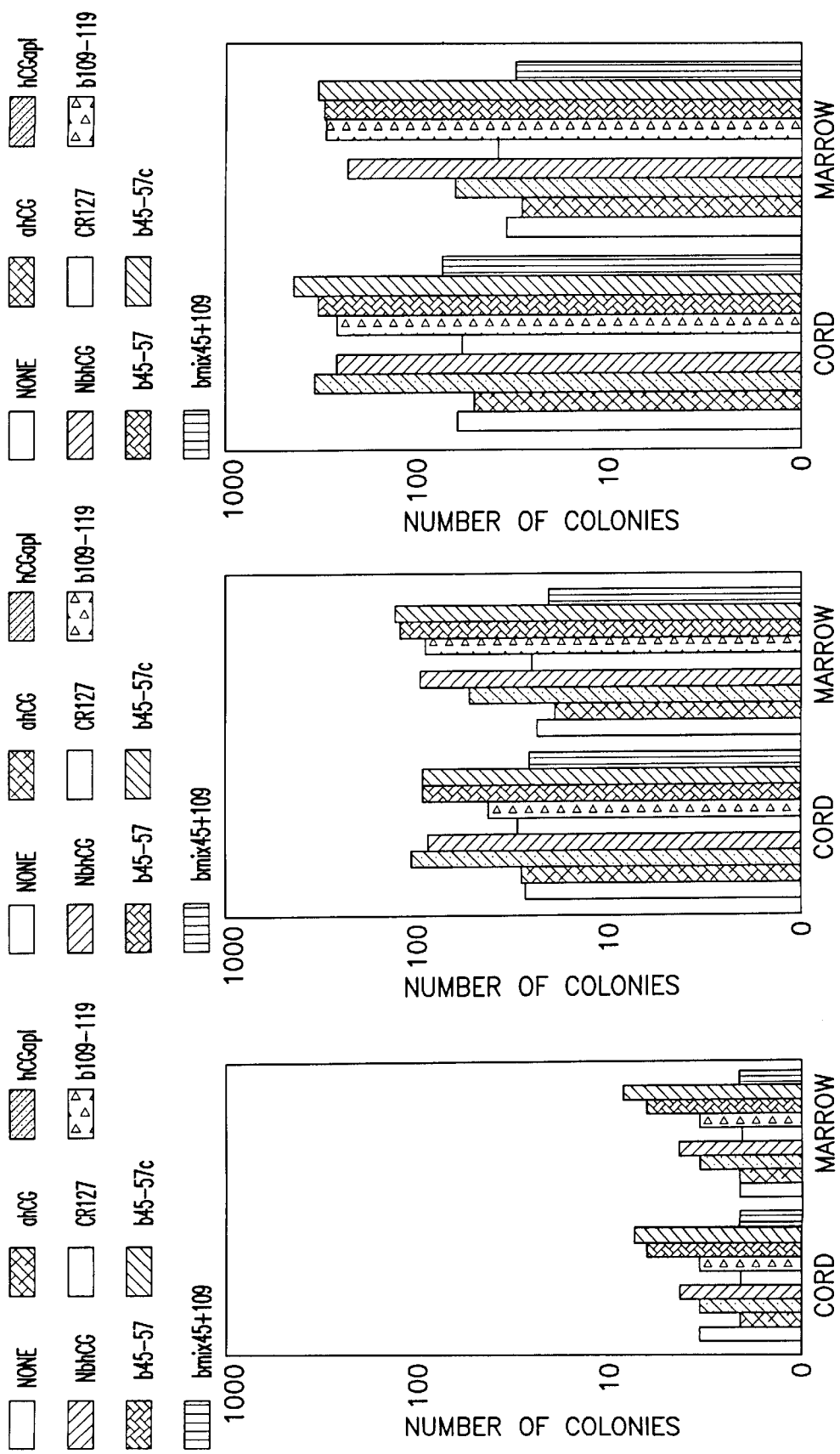

FIG. 4

| FIG.4A |
|--------|
| FIG.4B |
| FIG.4C |

FIG. 4A

```
AGACAAGGCA GGGGACGCAC CAAGG ATG GAG ATG TTC CAG GGG CTG CTG CTG     52
                            Met Glu Met Phe Gln Gly Leu Leu Leu
                            -20                         -15

TTG CTG CTG CTG AGC ATG GGC GGG ACA TGG GCA TCC AAG GAG CCG CTT    100
Leu Leu Leu Leu Ser Met Gly Gly Thr Trp Ala Ser Lys Glu Pro Leu
-10                      -5                       1

CGG CCA CGG TGC CGC CCC ATC AAT GCC ACC CTG GCT GTG GAG AAG GAG    148
Arg Pro Arg Cys Arg Pro Ile Asn Ala Thr Leu Ala Val Glu Lys Glu
              10                      15                      20
```

FIG.4B

```
GGC TGC CCC GTG TGC ATC ACC GTC AAC ACC ATC TGT GCC GGC TAC      196
Gly Cys Pro Val Cys Ile Thr Val Asn Thr Ile Cys Ala Gly Tyr
         25                  30                  35

TGC CCC ACC ATG ACC CGC GTG CTG CAG GGG GTC CTG CCG GCC CTG CCT  244
Cys Pro Thr Met Thr Arg Val Leu Gln Gly Val Leu Pro Ala Leu Pro
     40                  45                  50

CAG GTG TGC AAC TAC CGC GAT GTG CGC TTC GAG TCC ATC CGG CTC      292
Gln Val Cys Asn Tyr Arg Asp Val Arg Phe Glu Ser Ile Arg Leu
         55                  60                  65

CCT GGC TGC CCG CGC GGC CTG AAC CCC GTG GTC TCC TAC GCC GTG GCT  340
Pro Gly Cys Pro Arg Gly Leu Asn Pro Val Val Ser Tyr Ala Val Ala
     70                  75                  80                  85

CTC AGC TGT CAA TGT GCA CTC TGC CGC AGC ACC ACT GAC TGC GGG      388
Leu Ser Cys Gln Cys Ala Leu Cys Arg Arg Ser Thr Thr Asp Cys Gly
         90                  95                 100

GGT CCC AAG GAC CAC CCC TTG ACC TGT GAT GAC CCC CGC TTC CAG GAC  436
Gly Pro Lys Asp His Pro Leu Thr Cys Asp Asp Pro Arg Phe Gln Asp
    105                 110                 115
```

```
TCC TCT TCC TCA AAG GCC CCT CCC AGC CTT CCA AGC CCA TCC CGA          484
Ser Ser Ser Lys Ala Pro Pro Ser Leu Pro Ser Pro Ser Arg
        120                 125                 130

CTC CCG GGG CCC TCG GAC ACC CCG ATC CTC CCA CAA TAAAGGCTTC           530
Leu Pro Gly Pro Ser Asp Thr Pro Ile Leu Pro Gln
        135                 140                 145

TCAATCCGC                                                            539
```

FIG.4C

METHOD OF PROMOTING HEMATOPOIESIS USING DERIVATIVES OF HUMAN CHORIONIC GONADOTROPIN

1. CROSS REFERENCE TO RELATED APPLICATION

This application is a continuation in part of application Ser. No. 08/669,654, filed Jun. 24, 1996 now abandoned, which is incorporated by reference herein in its entirety.

2. FIELD OF THE INVENTION

The present invention is directed to methods of promoting hematopoiesis using human chorionic gonadotropin, the β-chain of human chorionic gonadotropin and peptides consisting of a sequence of a portion of the β-chain of human chorionic gonadotropin. The invention provides for methods of increasing production of hematopoietic cells in vitro and in vivo and methods for treating diseases and disorders associated with a reduction in hematopoietic cell numbers. The invention also provides pharmaceutical compositions and methods of administration.

3. BACKGROUND OF THE INVENTION

3.1. Hematopoietic Cell Production

The morphologically recognizable and functionally capable cells circulating in blood include erythrocytes, neutrophilic, eosinophilic, and basophilic granulocytes, B-, T-, non B-, non T-lymphocytes, and platelets. These mature hematopoietic cells derive from and are replaced, on demand, by morphologically recognizable dividing precursor cells for the respective lineages such as erythroblasts for the erythrocyte series, myeloblasts, promyelocytes and myelocytes for the granulocyte series, and megakaryocytes for the platelets. The precursor cells derive from more primitive cells that can simplistically be divided into two major subgroups: stem cells and progenitor cells (for review, see Broxmeyer, H. E., 1983, "Colony Assays of Hematopoietic Progenitor Cells and Correlations to Clinical Situations," *CRC Critical Reviews in Oncology/Hematology* 1:227–257). The definitions of stem and progenitor cells are operational and depend on functional, rather than on morphological, criteria. Stem cells have extensive self-renewal or self-maintenance capacity (Lajtha, L. G., 1979, *Differentiation* 14:23), a necessity since absence or depletion of these cells could result in the complete depletion of one or more cell lineages, events that would lead within a short time to disease and death. Some of the stem cells differentiate upon need, but some stem cells or their daughter cells produce other stem cells to maintain the precious pool of these cells. Thus, in addition to maintaining their own kind, pluripotential stem cells are capable of differentiation into several sub-lines of progenitor cells with more limited self-renewal capacity or no self-renewal capacity. These progenitor cells ultimately give rise to the morphologically recognizable precursor cells. The progenitor cells are capable of proliferating and differentiating along one, or more than one, of the myeloid differentiation pathways (Lajtha, L. G. (Rapporteur), 1979, *Blood Cells* 5:447).

A variety of infectious agents, genetic abnormalities and environmental factors can cause a deficiency in one or more hematopoietic cell types. For example, hematological abnormalities have been observed in HIV-1 infected individuals (the human immunodeficiency virus (HIV) has been implicated as the primary cause of the slowly degenerative immune system disease termed acquired immune deficiency syndrome (AIDS) (Barre-Sinoussi, F., et al., 1983, *Science* 220:868–870; Gallo, R., et al., 1984, *Science* 224:500–503)) particularly in the late stages of disease (Lunardi-Iskandar, Y. et al., 1989, *J. Clin. Invest* 83:610–615). These abnormalities include a reduction in $CD4^+$ T cells as well as cytopenias of one or more hematopoietic lineages, often associated with bone marrow morphologic abnormalities and deficient progenitor cell growth (Lunardi-Iskandar, Y. et al., 1989, *J. Clin. Invest* 83:610–615; Louache, F. et al., 1992, *Blood* 180:2991–2999). Idiopathic thrombocytopenic purpura (ITP), characterized by significant reduction in platelet numbers, often afflicts subjects infected with HIV (Ballem, P. J. et al., 1992, *N. Engl. J. Med.* 327:1779). The destruction of platelets in sufferers of ITP appears to be mediated by platelet associated autoantibodies (Berchtold, P. and Wenger, M., 1993, *Blood* 81:1246; Ballem, P. J. et al., 1987, *J. Clin. Invest.* 80:33). Thus, because management of ITP generally involves immunosuppression, treatment of ITP in HIV infected patients is complicated as administration of immunosuppressive drugs is extremely detrimental in HIV infection.

Additionally, chemotherapy and radiation therapy used in the treatment of cancer and certain immunological disorders can cause pancytopenias or combinations of anemia, neutropenia and thrombocytopenia. Thus, the increase or replacement of hematopoietic cells is often crucial to the success of such treatments. (For a general discussion of hematological disorders and their causes, see, e.g., "Hematology" in Scientific American Medicine, E. Rubenstein and D. Federman, eds., Volume 2, chapter 5, Scientific American, New York (1996)).

Furthermore, aplastic anemia presents a serious clinical condition as the overall mortality of all patients with aplastic anemias, in the absence of stem cell therapy, is high. Approximately 60–75% of individuals suffering from the disorder die within 12 months, in the absence of new stem cells. The overall incidence of these diseases is approximately 25 new cases per million persons per year. Although it is extremely unlikely that a single pathogenic mechanism accounts for all aplastic anemias, it is clear that provision of new hematopoietic stem cells is usually sufficient to allow permanent recovery, since transplantation of patients with aplastic anemia with bone marrow obtained from identical twins (i.e., syngeneic) (Pillow, R. P., et al., 1966, *N. Engl. J. Med.* 275:94–97) or from HLA-identical siblings (i.e., allogeneic) (Thomas, E. D., et al., Feb. 5, 1972, *The Lancet*, pp. 284–289) can fully correct the disease. However, some patients with aplastic anemia reject the transplanted marrow. This complication is particularly common among patients who have been immunologically sensitized as a result of multiple therapeutic blood transfusions.

The current therapy available for many hematological disorders as well as the destruction of the endogenous hematopoietic cells caused by chemotherapy or radiotherapy is bone marrow transplantation. However, use of bone marrow transplantation is severely restricted since it is extremely rare to have perfectly matched (genetically identical) donors, except in cases where an identical twin is available or where bone marrow cells of a patient in remission are stored in a viable frozen state. Except in such autologous cases, there is an inevitable genetic mismatch of some degree, which entails serious and sometimes lethal complications. These complications are two-fold. First, the patient is usually immunologically incapacitated by drugs beforehand, in order to avoid immune rejection of the foreign bone marrow cells (host versus graft reaction). Second, when and if the donated bone marrow cells become established, they can attack the patient (graft versus host disease), who is recognized as foreign. Even with closely matched family donors, these complications of partial mismatching are the cause of substantial mortality and morbidity directly due to bone marrow transplantation from a genetically different individual.

Peripheral blood has also been investigated as a source of stem cells for hematopoietic reconstitution (Nothdurtt, W., et al., 1977, *Scand. J. Haematol.* 19:470–481; Sarpel, S. C., et al., 1979, *Exp. Hematol.* 7:113–120; Ragharachar, A., et al., 1983, *J. Cell. Biochem. Suppl.* 7A:78; Juttner, C. A., et al., 1985, *Brit. J. Haematol.* 61:739–745; Abrams, R. A., et al., 1983, *J. Cell. Biochem. Suppl.* 7A:53; Prummer, O., et al., 1985, *Exp. Hematol.* 13:891–898). In some studies, promising results have been obtained for patients with various leukemias (Reiffers, J., et al., 1986, *Exp. Hematol.* 14:312–315; Goldman, J. M., et al., 1980, *Br. J. Haematol.* 45:223–231; Tilly, H., et al., Jul. 19, 1986, *The Lancet*, pp. 154–155; see also To, L. B. and Juttner, C. A., 1987, *Brit. J. Haematol.* 66: 285–288, and references cited therein); and with lymphoma (Korbling, M., et al., 1986, *Blood* 67:529–532). Other studies using peripheral blood, however, have failed to effect reconstitution (Hershko, C., et al., 1979, *The Lancet* 1:945–947; Ochs, H. D., et al., 1981, *Pediatr. Res.* 15:601). Studies have also investigated the use of fetal liver cell transplantation (Cain, G. R., et al., 1986, *Transplantation* 41:32–25; Ochs, H. D., et al., 1981, *Pediatr. Res.* 15:601; Paige, C. J., et al., 1981, *J. Exp. Med.* 153:154–165; Touraine, J. L., 1980, *Excerpta Med.* 514:277; Touraine, J. L., 1983, *Birth Defects* 19:139; see also Good, R. A., et al., 1983, *Cellular Immunol.* 82:44–45 and references cited therein) or neonatal spleen cell transplantation (Yunis, E. J., et al., 1974, *Proc. Natl. Acad. Sci. U.S.A.* 72:4100) as stem cell sources for hematopoietic reconstitution. Cells of neonatal thymus have also been transplanted in immune reconstitution experiments (Vickery, A. C., et al., 1983, *J. Parasitol.* 69(3):478–485; Hirokawa, K., et al., 1982, *Clin. Immunol. Immunopathol.* 22:297–304).

Clearly, there is a tremendous need for methods of expanding blood cells in vitro or therapies which increase the production of hematopoietic cells in vivo.

3.2. Human Chorionic Gonadotropin

Human chorionic gonadotropin (hCG), which is required for the maintenance of pregnancy, is a member of the glycoprotein hormone family. The glycoprotein hormones, which also include follicle-stimulating hormone (FSH), luteinizing hormone (LH) and thyroid-stimulating hormone (TSH), consist of two sub-units, $\alpha$ and $\beta$. These subunits are non-covalently linked to form a heterodimer, and heterodimer formation has been shown to be required for receptor binding. Within a particular species, the $\alpha$-subunits are identical among the glycoprotein hormones while the $\beta$-subunits differ and determine the receptor binding specificity of the particular hormone (Kornyei, J. L., et al., 1993, *Biol. Reprod.* 49:1149). The $\beta$-subunits of the glycoprotein hormones exhibit a high degree of sequence similarity within the N-terminal 114 amino acids. LH is the most similar to hCG with 85% sequence homology within the first 114 amino acids, and both proteins bind the same receptor. hCG, however, contains a C-terminal extension not present in the other glycoprotein $\beta$-chains (Lapthorn, A. J., et al., 1994, *Science* 369:455–461).

From the three dimensional crystal structure of hCG, it was determined that hCG, like the growth factors nerve growth factor (NGF), transforming growth factor-$\beta$ (TGF-$\beta$) and platelet derived growth factor-$\beta$ (PDGF-$\beta$), is a cysteine-knot glycoprotein. Proteins containing such a cysteire-knot motif have at least three disulfide bridges, two of which join adjacent anti-parallel strands of the peptide, thus, forming a ring, and one of which joins the peptide chain through the ring. Particular structures in the hCG $\beta$-chain include the determinant loop sequence ($\beta$93–100) which has been implicated in subunit association and the longest inter-cysteine loop ($\beta$38–57) which may play a role in receptor binding. Residues 47–53 appear to be exposed at the surface of this inter-cysteine loop (Lapthorn et al., 1994, *Nature* 369:455–461).

Harris, P. J. (1995, *The Lancet* 346:118–119) found that administration of hCG preparations to certain HIV infected subjects led to, among other improvements in symptoms of AIDS, increases in $CD4^+$ and $CD8^+$ T cell lymphocytes.

Citation of references hereinabove shall not be construed as an admission that such references are prior art to the present invention.

4. SUMMARY OF THE INVENTION

The present invention relates to therapeutic methods and compositions for treatment and prevention of diseases and disorders in which an increase in one or more types of hematopoietic cells is desirable. The therapeutic compounds of the invention are hCG, $\beta$-hCG and proteins consisting of a sequence of a portion of $\beta$-hCG, and related derivatives and analogs. The invention provides for treatment and prevention of diseases and disorders (e.g., involving hematopoietic cell deficiencies) by administration either of a therapeutic compound of the invention or of hematopoietic cells, the numbers of which have been increased in vitro by contact with a therapeutic compound of the invention. The invention thus also provides in vitro methods of expanding hematopoietic cells. The therapeutic compounds of the invention include: hCG, $\beta$-hCG, therapeutically and prophylactically effective peptides containing a sequence of a portion of $\beta$-hCG, derivatives and analogs of hCG, $\beta$-hCG, and therapeutically and prophylactically effective peptides containing a sequence of a portion of $\beta$-hCG, and nucleic acids encoding hCG, $\beta$-hCG and therapeutically and prophylactically effective peptides having a sequence of a portion of $\beta$-hCG, and derivatives and analogs of the foregoing. In a specific embodiment, gene therapy methods are provided using hCG, $\beta$-hCG and therapeutically and prophylactically effective $\beta$-hCG peptides to induce proliferation of hematopoietic progenitor or stem cells into which cells a nucleic acid of interest is introduced either before or after proliferation. The proliferation induced by the methods of the invention can be with or without concomitant hematopoietic cell differentiation, and, in a preferred embodiment, is proliferation followed by differentiation of the cells. In a preferred embodiment, the therapeutic comprises a $\beta$-hCG peptide, the amino acid sequence of which consists of amino acid numbers 41–54, 45–54, 47–53, 45–57 and 109–119 (SEQ ID NOS:3–7, respectively) of the $\beta$-hCG sequence depicted in FIG. 4 (a portion of SEQ ID NO:2).

The invention further provides assays, both in vitro and in vivo, for testing the efficacy of the Therapeutics of the invention.

The invention also provides methods of administration and pharmaceutical compositions containing a Therapeutic of the invention.

4.1. Definitions and Abbreviations

As used herein, the following abbreviations will have the meanings indicated:

AIDS=Acquired Immune Deficiency Syndrome

ARC=AIDS Related Complex

BFU-E=burst forming unit-erythroid. A hematopoietic progenitor cell which is capable of producing a colony of erythroid progeny cells in semi-solid medium.

CFU=colony forming unit. A cell which is capable of producing a colony of progeny cells in semi-solid medium.

CFU-GEMM=colony forming unit-granulocyte, erythrocyte, monocyte/macrophage, megakaryocyte. A multipotential hematopoietic progenitor cell which is capable of producing a colony composed of granulocyte, erythrocyte, monocyte/macrophage, and megakaryocyte progeny in semi-solid medium.

CFU-GM=colony forming unit-granulocyte, macrophage. A hematopoietic progenitor cell which is capable of producing a colony composed of granulocyte and macrophage progeny in semi-solid medium.

CFU-MK=colony forming unit-megakaryocyte. A hematopoietic progenitor cell which is capable of producing a colony composed of megakaryocyte progeny in semi-solid medium.

CFU-S=colony forming unit-spleen. A multipotential stem cell with self-renewal capacity, which, upon inoculation into a lethally irradiated mouse, is capable of producing a colony (module) on the spleen. CFU-S is not a marrow-repopulating cell; it is a less primitive stem cell which does not provide long-term engraftment in an animal.

CSF=colony stimulating factor

Epo=erythropoietin

FBS=fetal bovine serum. Also known as fetal calf serum.

G-CSF=granulocyte colony stimulating factor

GM-CSF=granulocyte-macrophage colony stimulating factor hCG=Human Chorionic Gonadotropin HIV=Human Immunodeficiency Virus ITP=Idiopathic thrombocytopenic purpura (a severe platelet deficiency)

PB=peripheral blood

PBMC=Peripheral Blood Mononuclear Cells

5. DESCRIPTION OF THE FIGURES

FIGS. 1A–D. Effects of an hCG preparation on indicators of SIV infection in SIV-infected macaques. SIV was given intravenously at a dose of $10^{4.5}$ TCID$_{50}$ per ml. (A) SIV titer was monitored over time in months by quantifying the p27 gag protein (Organon Teknika assay) as nanograms (ng) of p27/ml of plasma from the plasma of the SIV infected macaques. Treated SIV-infected macaques (indicated as Rx) were given hCG APL, 3000 IU 2× weekly. Plasma levels of p27 gag in these treated monkeys are indicated on the graph by lines with diamonds, number (#) signs or filled circles. Results with the untreated SIV-infected macaques (indicated UnRx) are indicated by the lines with either stars or triangles. (B) CD4$^+$ T cell levels were determined in cells/mm$^3$ in SIV-infected macaques either treated with hCG or untreated over time in months. Results from the SIV-infected monkeys treated with hCG (APL) (Rx) are indicated by lines with diamonds, number (#) signs or filled circles, while results with the untreated monkeys (UnRx) are indicated by lines with stars or triangles. (C) Change in weight in kilograms (kg) was monitored in treated and untreated SIV-infected monkeys over time in months. Weight changes in the SIV-infected monkeys treated with hCG (APL) (Rx) are indicated by lines with diamonds, # signs or filled circles, while results in the untreated monkeys (UnRx) are indicated by lines with stars or triangles. (D) Levels of CD4$^+$ T cells were monitored in normal uninfected monkeys either treated with hCG (APL) or untreated over time in months. CD4$^+$ T cell levels in the untreated monkeys are indicated by lines with sun-like figures or squares, and the results in the treated monkeys are indicated by lines with pentagonal figures or with filled inverted triangles.

FIGS. 2A–F. Effects of some hCG preparations on HIV-1 viral load, CD4$^+$ T cell levels, and weight over extended periods in individual patients with advanced HIV infection. (A and B) Bar graphs depicting the results from hCG treatment of patient PH-VE (see Table 2) over time in weeks. (A) Graph presents data of CD4$^+$ T cell count in mm$^3$ (line with diamonds) and viral load as copies×1000/ml plasma (line with circles). (B) Graph documents the status of the patient's Kaposi's sarcoma with respect to the dosages of hCG administered, indicated as IU×1000/week. At week 0, intralesional therapy began; at week 3, regression of KS lesions was observed; at week 68, KS lesions recurred and at week 79, KS lesion regression was observed. (C and D) Bar graphs depicting the results of hCG treatment of patient PH-SPBE (see Table 2) over time in weeks. (C) Graph presents data of CD4$^+$ T cell count in mm$^3$ (line with diamonds) and viral load as copies (×1000)/ml plasma (line with circles). (D) Bar graph indicates the dosage of hCG per week in IU×1000. It is noted under the graph that ritonavir therapy was begun at 20 weeks of therapy. (E and F) Bar graphs depicting the results from hCG treatment of patient PH-VE (see Table 2) over time in weeks. (E) Graph presents data of CD4$^+$ T cell count in mm$^3$ (line with diamonds) and viral load as copies (×1000)/mL plasma (line with circles). (F) Bar graph indicates the dosage of hCG per week in IU×1000. It is noted under the graph that ritonavir therapy was begun after 20 weeks of therapy.

FIGS. 3A–C. These bar graphs demonstrate the effects of hCG preparations and peptides on hematopoiesis in vitro. (A) This bar graph depicts results of colony assays in terms of number of colonies for CFU-MIX (colony forming units of megakaryocytes, erythrocytes, granulocytes and monocytes). (B) This bar graph presents data from colony assays for BFU-e (Burst forming units of erythrocytes) in terms of number of colonies. (C) This bar graph presents results from colony assays of CFU-GM (colony forming units of granulo-macrophages) in terms of number of colonies. For all three graphs, results are shown for cells isolated from cord blood ("cord") and bone marrow ("marrow"). The results are averages of 3 sets of results with less than 10% variation and are representative of multiple experiments. The results from no treatment are indicated by open bars; the results with α-hCG are represented by solid bars; the results with hCG-APL (hCGapl) are represented by bars with a lattice pattern; the results with native β-hCG preparation (NbhCG) are represented by cross-hatched bars; the results with the highly purified hCG preparation (CR127) are represented by open bars; the results with the β-hCG peptide of amino acids 109–119 (SEQ ID NO:7) (b109–119) are shown by the diagonally stippled bars; the results with the β-hCG peptide of amino acids 45–57 (SEQ ID NO:6) (b45–57) are shown by the bars with the diamonds; the results with the circularized β-hCG peptide of amino acids 44–57 (SEQ ID NO:12) with cysteine substituted for the amino acid at position 44 (b45–57c) are represented by the diagonally striped bars; and the results with the mixture of scrambled β-hCG peptides of amino acids 45–57 and 109–119 (bmix45+109) are represented by the vertically striped bars.

FIG. 4. Nucleotide (SEQ ID NO:1) and amino acid (SEQ ID NO:2) sequences of β-hCG.

Figure 5A:
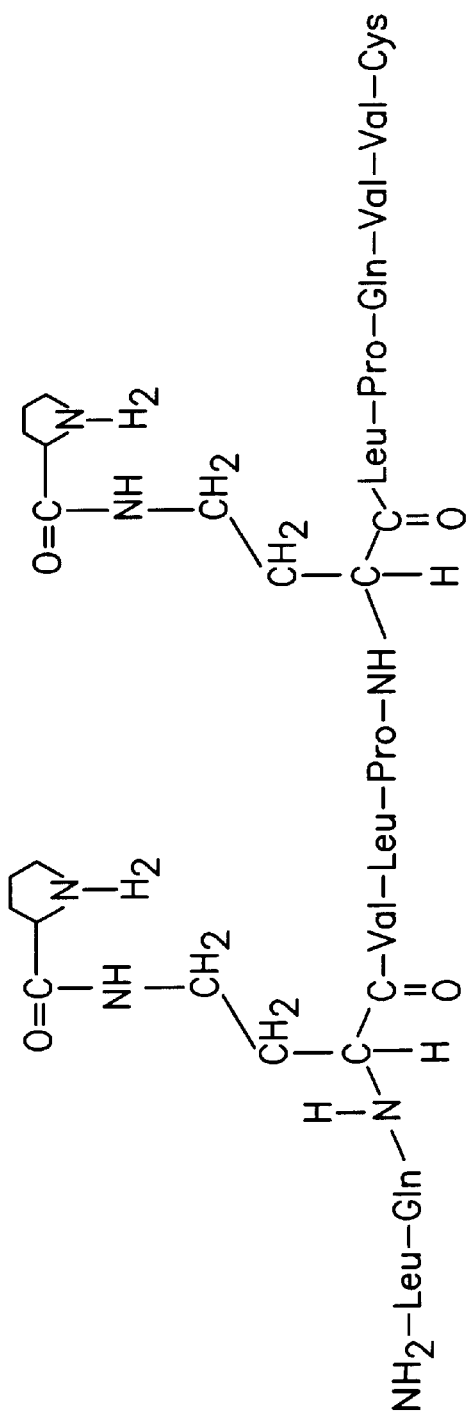

FIGS. 5A and B. Schematic depiction of the structures of (A) the linear peptide of amino acids 45–57 (SEQ ID NO:6) of the β-hCG sequence depicted in FIG. 4 (SEQ ID NO:2) where the amino acid residues at positions 47 and 51 are substituted by a branch made up of diaminobutyric acid peptide bonded to proline, and (B) the circularized peptide of amino acids 44–57 (SEQ ID NO:12) with valine at position 44 substituted with cysteine, which protein is circularized via a disulfide bond between its amino- and carboxy-terminal cysteines. In both A and B, amino acids are represented by their three letter amino acid code, except for the branched residues and the terminal cysteines, for which the structure is depicted.

6. DETAILED DESCRIPTION OF THE INVENTION

The present invention relates to therapeutic methods and compositions for treatment and prevention of diseases and disorders in which increased amounts of hematopoietic cells are desirable (e.g., disorders associated with reduced numbers of one or more hematopoietic cell types) by administration of hCG, β-hCG and therapeutically or prophylactically effective proteins (e.g., peptides) having a sequence of a portion of β-hCG (β-hCG peptides), and derivatives and analogs thereof. The invention provides for treatment and prevention of hematopoietic cell deficiencies by administration either of a therapeutic compound of the invention or of hematopoietic cells, the numbers of which have been increased in vitro by contact with a therapeutic compound of the invention. The invention also provides methods for expansion of hematopoietic cells in vitro by contact with a Therapeutic of the invention. The therapeutic compounds of the invention include: hCG, β-hCG, therapeutically or prophylactically effective β-hCG peptides, derivatives and analogs of hCG, β-hCG, or β-hCG peptides and nucleic acids encoding β-hCG and therapeutically and prophylactically effective β-hCG peptides, and analogs and derivatives thereof.

In a preferred embodiment, a therapeutic composition of the invention comprises a β-hCG peptide, the amino acid sequence of which consists of amino acid numbers 41–53, 42–53, 43–53, 44–53, 44–57, 45–53, 46–53, 45–54, 45–55, 45–56, 45–58, 47–54, 47–55, 47–56, 47–58, 48–145, 58–145 or 109–145 (SEQ ID NOS:8–25, respectively) of FIG. 4 (a portion of SEQ ID NO:2), particularly a β-hCG peptide which consists of amino acid numbers 41–54, 45–54 or 109–119 (SEQ ID NOS:3, 4, or 7, respectively), most preferably of a β-hCG peptide which consists of amino acids 47–53 (SEQ ID NO:5) or 45–57 (SEQ ID NO:6). In other preferred embodiments, the therapeutic comprises a β-hCG peptide, the amino acid sequence of which consists of circularized (via a disulfide bond between its amino- and carboxy- terminal cysteines) 44–57 (SEQ ID NO:26) with the valine at position 44 substituted with cysteine ((Val44Cys) 45–57 circularized) (depicted in FIG. 5B), 45–57 (SEQ ID NO:6) where the amino acid residues at positions 47 and 51 are substituted by a branch, where the branches are made up of diaminobutyric acid peptide bonded to a proline residue (depicted in FIG. 5A). The amino acid sequence of β-hCG is depicted in FIG. 4 (SEQ ID NO:2).

For clarity of disclosure, and not by way of limitation, the detailed description of the invention is divided into the subsections which follow.

6.1. Therapeutic Uses

The invention provides for treatment or prevention of diseases and disorders in which increased numbers of one or more hematopoietic cell types are desirable (e.g., diseases or disorders associated with one or more hematopoietic cell deficiencies) by administration of a therapeutic compound (termed herein "Therapeutic") of the invention or by administration of hematopoietic cells, the production of which has been induced in vitro by contacting the cells with a Therapeutic of the invention. Such "Therapeutics" include but are not limited to: hCG, β-hCG and derivatives thereof, and therapeutically or prophylactically effective β-hCG peptides, i.e., those peptides which prevent or treat hematopoietic deficiencies (e.g., as demonstrated in in vitro and in vivo assays described infra) as well as modifications, derivatives and analogs thereof and nucleic acids encoding hCG, β-hCG and therapeutically and prophylactically effective β-hCG peptides, and derivatives and analogs thereof. In one embodiment, the Therapeutic of the invention is a protein containing an amino acid sequence of a therapeutically and prophylactically effective portion of β-hCG. In a preferred embodiment, the Therapeutic of the invention is a protein having a sequence of amino acid numbers 41–54, 45–54, 47–53 or 45–57 (SEQ ID NOS:3–6, respectively) of the β-hCG sequence depicted in FIG. 4 (a portion of SEQ ID NO:2). In other embodiments, the Therapeutic of the invention is a protein having a sequence of amino acid numbers 41–53, 42–53, 43–53, 44–53, 44–57, 45–53, 46–53, 45–54, 45–55, 45–56, 45–58, 47–54, 47–55, 47–56, 47–58, 48–145, 58–145, 109–119 or 109–145 (SEQ ID NOS:8–24, 7 and 25, respectively) of the β-hCG sequence of FIG. 4 (a portion of SEQ ID NO:2). Additionally, the present inventors have found that different preparations of hCG and β-hCG have variable effects on hematopoietic cell proliferation in vitro and in vivo. Specifically, the inventors found that among the (non-recombinant) commercial preparations they investigated, hCG from Fujisawa was the most effective, hCG from APL (Wyeth-Ayerst) the next most effective, and pregnyl (Organon) the next most effective. hCG preparations can be screened for utility in inducing hematopoiesis in vitro or in vivo by the methods described infra in Section 5.4 or any method known in the art.

In one embodiment of the invention, the Therapeutic is administered directly to a patient suffering from a disease or disorder amenable to treatment by increasing production of one or more hematopoietic cell types (e.g., a disease or disorder associated with a hematopoietic cell deficiency). In another embodiment of the invention, hematopoietic cells, preferably stem and/or progenitor cells, are obtained, contacted with a Therapeutic of the invention in vitro to induce proliferation of the cells, and then administered to a subject suffering from a disease or disorder associated with a hematopoietic cell deficiency. Preferably, autologous hematopoietic cells (obtained from the subject or its identical twin) are reintroduced into the subject after in vitro expansion. In this embodiment, gene therapy methods can be performed by introducing a nucleic acid of interest, e.g., containing a gene which provides a function desired in a subject, into the hematopoietic cells, before or after expansion of the cells by contact with a Therapeutic. Hematopoietic cell subpopulations can be isolated for use, before or after expansion in vitro. For example, blood cells can be isolated and expanded, and optionally also differentiated, in vitro, followed by introduction of all or a portion of the cells (e.g, purified platelets, red blood cells, lymphocytes, etc.) into a patient.

In general, disorders that can be treated by methods of the invention include, but are not limited to, five broad categories. First are diseases resulting from a failure or dysfunction of normal blood cell production and maturation (i.e., aplastic anemia, cytopenias and hypoproliferative stem cell disorders). The second group are neoplastic, malignant diseases in the hematopoietic organs (e.g., leukemia and lymphomas). The third group of disorders comprises those of patients with a broad spectrum of malignant solid tumors of non-hematopoietic origin. Induction of hematopoietic cell proliferation or administration of replacement hematopoietic cells in these patients serves as a bone marrow rescue procedure, which is provided to a patient following otherwise lethal chemotherapy or irradiation of the malignant tumor. The fourth group of diseases consists of autoimmune conditions, where the hematopoietic cells serve as a source of replacement of an abnormal immune system. The fifth group of diseases comprises a number of genetic disorders which can be corrected by infusion of hematopoietic stem cells, preferably syngeneic, which prior to transplantation have undergone gene therapy. Particular diseases and disorders which can be treated by induction of hematopoietic cell production in vivo or by administration of hematopoietic cells expanded in vitro include but are not limited to those listed in Table 1, and described infra.

TABLE 1

DISEASES OR DISORDERS WHICH CAN BE TREATED
BY INCREASING PRODUCTION OF HEMATOPOIETIC CELLS

I. Diseases resulting from a failure or dysfunction of normal blood cell production and maturation hyperproliferative stem cell disorders
aplastic anemia
pancytopenia
agranulocytosis
thrombocytopenia
red cell aplasia
Blackfan-Diamond syndrome
due to drugs, radiation, or infection
idiopathic II. Hematopoietic malignancies acute lymphoblastic (lymphocytic) leukemia
chronic lymphocytic leukemia
acute myelogenous leukemia
chronic myelogenous leukemia
acute malignant myelosclerosis
multiple myeloma
polycythemia vera
agnogenic myelometaplasia
Waldenstrom's macroglobulinemia
Hodgkin's lymphoma
non-Hodgkin's lymphoma III. Immunosuppression in patients with malignant, solid tumors malignant melanoma
carcinoma of the stomach
ovarian carcinoma
breast carcinoma
small cell lung carcinoma
retinoblastoma
testicular carcinoma
glioblastoma
rhabdomyosarcoma
neuroblastoma
Ewing's sarcoma
lymphoma IV. Autoimmune diseases rheumatoid arthritis
diabetes type I
chronic hepatitis
multiple sclerosis
systemic lupus erythematosus V. Genetic (congenital) disorders anemias
familial aplastic
Fanconi's syndrome
Bloom's syndrome
pure red cell aplasia (PRCA)
dyskeratosis congenita
Blackfan-Diamond syndrome TABLE 1-continued DISEASES OR DISORDERS WHICH CAN BE TREATED
BY INCREASING PRODUCTION OF HEMATOPOIETIC CELLS congenital dyserythropoietic syndromes I–IV
Chwachmann-Diamond syndrome
dihydrofolate reductase deficiencies
formamino transferase deficiency
Lesch-Nyhan syndrome
congenital spherocytosis
congenital elliptocytosis
congenital stomatocytosis
congenital Rh null disease
paroxysmal nocturnal hemoglobinuria
G6PD (glucose-6-phosphate dehydrogenase)
variants 1,2,3
pyruvate kinase deficiency
congenital erythropoietin sensitivity
deficiency
sickle cell disease and trait
thalassemia alpha, beta, gamma
met-hemoglobinemia
congenital disorders of immunity
severe combined immunodeficiency disease (SCID)
bare lymphocyte syndrome ionophore-responsive combined immunodeficiency
combined immunodeficiency
with a capping abnormality
nucleoside phosphorylase deficiency
granulocyte actin deficiency
infantile agranulocytosis
Gaucher's disease
adenosine deaminase deficiency
Kostmann's syndrome
reticular dysgenesis
congenital leukocyte dysfunction syndromes VI. Others osteopetrosis
myelosclerosis
acquired hemolytic anemias
acquired immunodeficiencies
infectious disorders causing primary or secondary immunodeficiencies bacterial infections (e.g. Brucellosis, Listeriosis, tuberculosis, leprosy)
parasitic infections (e.g. malaria, Leishmaniasis)
fungal infections
disorders involving disproportions in lymphoid cell sets and impaired immune functions due to aging
phagocyte disorders Kostmann's agranulocytosis
chronic granulomatous disease
Chediak-Higachi syndrome
neutrophil actin deficiency
neutrophil membrane GP-180 deficiency
metabolic storage diseases mucopolysaccharidoses
mucolipidoses
miscellaneous disorders involving immune mechanisms
Wiskott-Aldrich Syndrome
alpha 1-antitrypsin deficiency

6.1.1. Diseases Resulting from a Failure or Dysfunction of Normal Blood Cell Production and Maturation In a preferred aspect, a Therapeutic of the invention is used to treat a disease resulting from a failure or dysfunction of normal blood cell production and maturation, such as an aplastic anemia, a cytopenia or a hypoproliferative stem cell disorder. These disorders entail failure of stem cells in bone marrow to provide normal numbers of functional blood cells. The aplastic anemias result from the failure of stem cells to give rise to the intermediate and mature forms of red cells, white cells, and platelets. While red cell production is usually most seriously affected, a marked decrease in production of other mature blood cell elements is also seen as some anemias specifically affect production of white cells and/or platelets. The large majority of these anemias are acquired during adult life, and do not have any apparent genetic predisposition. About half of these acquired anemias arise in the absence of any obvious causative factor such as exposure to poisons, drugs or disease processes that impair stem cell function; these are termed idiopathic aplastic anemias. The remaining cases are associated with exposure to an extremely diverse array of chemicals and drugs and also occur as the consequence of viral infections, such as HIV infection, and after pregnancy. Other specific types of aplastic anemia are termed agranulocytosis or thrombocytopenia to indicate that the major deficiency lies in particular white cells or in platelet production, respectively. These non red blood cell deficiencies are also often associated with HIV infection. Also significantly associated with HIV infection is a severe platelet deficiency, Idiopathic Thrombocytopenic Purpura (ITP). Additionally, agranulocytosis may be associated with autoimmune syndromes such as systemic lupus erythematosus (SLE) or with other infections, such as neonatal rubella.

In addition, immune deficiencies which are the primary or secondary result of infection by pathogenic microorganisms can be treated by administration of a Therapeutic of the invention. For example, immune deficiencies caused by microorganisms which are intracellular pathogens of hematopoietic cells, can be treated by the provision of new hematopoietic cells. These new hematopoietic cells can be generated by contacting hematopoietic stem and/or progenitor cells in vitro with a Therapeutic of the invention to cause proliferation of the cells. Microorganisms causing immune deficiencies which may be treated according to this embodiment of the invention include but are not limited to gram-negative bacilli such as Brucella or Listeria, the mycobacterium which are the etiological agents of tuberculosis or of Hansen's disease (leprosy), parasites such as Plasmodium (the etiological agents of malaria) or Leishmania, and fungi (such as those that cause pneumonia and other lethal infections secondary to immunodeficiencies) (for a discussion of many of these disorders, see Harrison's Principles of Internal Medicine, 1970, 6th Edition, Wintrobe, M. M., et al., eds., McGraw-Hill, New York, pp. 798–1044).

In a preferred embodiment of the invention, a Therapeutic of the invention is administered for the treatment of a cytopenia associated with HIV infection. The hematopoietic deficiencies associated with HIV infection include reduction in $CD4^+$ T cells and other lymphocytes, red blood cells, platelets, specifically ITP, and neutrophils. Such a disorder is treated by contacting hematopoietic stem and/or progenitor cells in vitro with a Therapeutic of the invention and then infusing the resulting hematopoietic cells into the subject in need of treatment. In a another preferred embodiment, the disorder is treated by direct administration of a Therapeutic of the invention to the subject in need of treatment. Assays for determining the efficacy of particular Therapeutics for treatment of hematopoietic deficiencies associated with HIV infection are detailed in Section 5.4 infra.

6.1.2. Treatment of Malignancies

Hyperproliferative malignant stem cell disorders as well as non-hematopoietic malignancies can be treated with chemotherapy or radiation therapy along with rescue of hematopoietic cells by direct administration of a Therapeutic of the invention or by administration of hematopoietic cells induced to proliferate by contacting the cells with a Therapeutic of the invention. The conditions that can be treated according to the invention include, but are not limited to, the leukemias listed in Table 1 and the solid tumors listed in Table 1.

These malignancies are currently treated by, inter alia, chemotherapy and, when feasible, allogeneic bone marrow transplantation. However, allogeneic HLA identical sibling bone marrow is available only to less than one-third of patients, and this treatment is associated with transplantation-related complications such as immunodeficiency and graft versus host disease. Induction of hematopoietic cell proliferation in vivo or provision of autologous hematopoietic stem and progenitor cells expanded by administration of a Therapeutic in vitro permits hematopoietic reconstitution of patients lacking suitable allogeneic donors and eliminates the risks of graft versus host disease arising from allogeneic marrow transplantation. Thus, in a specific embodiment, a Therapeutic is used to induce proliferation in hematopoietic cells which are then administered to a patient who has undergone chemotherapy or radiation therapy for treatment of cancer or an immunological disorder. In another embodiment, a Therapeutic is directly administered to a patient who has undergone chemotherapy or radiation therapy for treatment of cancer or an immunological disorder.

6.1.3. Autoimmune Disorders

Many chronic inflammatory and degenerative diseases are characterized by a continuous immune reaction against the body's own tissues. Such autoimmune disorders include but are not limited to rheumatoid arthritis and other inflammatory osteopathies, diabetes type I, chronic hepatitis, multiple sclerosis, and systemic lupus erythematosus. Autoimmune disorders are often treated by lymphoid irradiation. Administration of a Therapeutic of the invention or of cells produced by exposure to a Therapeutic in vitro can be valuable to repopulate the hematopoietic system after radiotherapy.

Anti-inflammatory drugs such as steroids retard the inflammatory cells which are activated by autoreactive T cells, but do not prevent T cells which recognize self-proteins from activating new inflammatory cells. A more direct approach to treating autoimmune diseases depends on eradication of T cells by irradiation of the lymphoid tissues, and relying on stem cells from the unirradiated bone marrow to repopulate the patient's hematopoietic system. The rationale is that the formation of new populations of mature T cells from bone marrow stem cells may result in absence of T cells that have reactivity to self-specific antigens. This procedure, called total lymphoid irradiation (TLI), has been used to treat intractable rheumatoid arthritis (Strober, S., et al., 1985, *Annals of Internal Medicine* 102:441–449, 450–458). These clinical trials showed that in the majority of otherwise intractable cases, joint disease was significantly alleviated for at least 2–3 years. However, the major drawback to such treatment is failure of stem cells in the bone marrow of these elderly patients to efficiently repopulate the hematopoietic system, resulting in infections and bleeding disorders. Analogous studies have been made of the effects of TLI as an alternative to cytotoxic drugs for treatment of SLE (Strober, S., et al., 1985, *Ann. Internal Med.* 102:450). Studies of the use of TLI to treat intractable SLE have also shown that this treatment alleviates disease activity, but is severely limited by failure of bone marrow stem cells to rapidly and efficiently repopulate the hematopoietic system after irradiation.

Thus, a Therapeutic of the invention can be administered to promote proliferation of the remaining hematopoietic cells to increase the success of TLI therapy. Additionally, hematopoietic stem and progenitor cells can be isolated from the patient before treatment, induced to proliferate in vitro and then introduced into the patient after TLI treatment to repopulate the hematopoietic system.

6.1.4. Gene Therapy

Administration of hematopoietic, preferably hematopoietic stem and progenitor, cells which have been induced to proliferate with a Therapeutic of the invention and have undergone gene therapy, i.e., which have stably incorporated a heterologous gene capable of expression by their progeny cells, can be of great value in the treatment of diseases and disorders affecting cells of hematopoietic lineage. In one embodiment, hematopoietic reconstitution with such recombinant hematopoietic cells can be used in the treatment of genetic disorders of the hematopoietic system. Such genetic disorders include but are not limited to those listed in Table 1, supra. Genetic deficiencies or dysfunctions of hematopoietic cells can be treated by supplying, to a patient, recombinant stem and progenitor cells. In a specific embodiment, patients who have hematopoietic cells which lack a gene or have a mutant gene, can be provided stem and progenitor cells that have incorporated a functional counterpart of the deficient gene. In particular, such genes which can be subject to gene therapy include but are not limited to hemoglobin or enzymes which mediate its synthetic pathway (e.g., for treatment of anemias such as beta-thalassemia, sickle-cell disease).

In another specific embodiment, patients with infections by pathogenic microorganisms which occur in or affect a hematopoietic cell lineage can be treated with recombinant hematopoietic cells. Such recombinant hematopoietic cells can contain a heterologous gene which is expressed as a product which ameliorates disease symptoms, is toxic to the pathogen without significant detriment to the host, or interferes with the pathogen's life cycle, etc. Pathogens which cause infections which may be treated with recombinant stem cells according to this embodiment of the invention include but are not limited to lymphotropic viruses such as HIV, gram-negative bacilli such as Brucella or Listeria; the mycobacterium which cause tuberculosis or which cause Hansen's disease (leprosy); parasites such as Plasmodium (the etiological agents of malaria), or Leishmania; and fungi (such as those that cause pneumonia and other lethal infections secondary to immunodeficiencies) (for a discussion of many of these disorders, see Harrison's Principles of Internal Medicine, 1970, 6th Edition, Wintrobe, M. M., et al., eds., McGraw-Hill, New York, pp. 798–1044).

As a particular embodiment, it is possible to construct recombinant stem or progenitor cells that express a sequence which is "anti-sense" to the nucleic acid of a hematopoietic cell pathogen. Such a sequence, which is complementary to the pathogen's RNA or DNA, can hybridize to and inactivate such RNA or DNA, inhibiting the function or expression of the nucleic acid and disrupting the pathogen's life cycle. As a particular example, recombinant hematopoietic cells can be used in the treatment of AIDS. Recombinant stem and progenitor cells which express an anti-sense nucleic acid that is complementary to a critical region (e.g., the long-terminal repeat or polymerase sequence) of the HIV genome (Wain-Hobson et al., 1985, Cell 40:9–17) can be used for hematopoietic reconstitution for the treatment of AIDS.

Many methods of gene therapy are available in the art (for general reviews of the methods of gene therapy, see Goldspiel et al., 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIBTECH 11(5): 155–215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred aspect, the nucleic acid which provides a gene product desired in a subject is introduced into an expression vector that produces the gene product. In particular, such a nucleic acid has a promoter operably linked to the nucleic acid sequence of interest, said promoter being inducible or constitutive, and, optionally, tissue-specific. In another particular embodiment, a nucleic acid molecule is used in which the sequences of interest are flanked by regions that promote homologous recombination at a desired site in the genome, thus providing for intrachromosomal expression of the desired protein (Koller and Smithies, 1989, Proc. Natl. Acad. Sci. USA 86:8932–8935; Zijlstra et al., 1989, Nature 342:435–438).

In an embodiment of the invention, the nucleic acid is introduced into a hematopoietic cell that is then expanded by exposure to a Therapeutic of the invention prior to administration in vivo of the resulting recombinant cell. Alternatively, the nucleic acid can be introduced after expansion. Such introduction can be carried out by any method known in the art, including, but not limited to, transfection, electroporation, microinjection, infection with a viral vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, 1993, Meth. Enzymol. 217:599–618; Cohen et al., 1993, Meth. Enzymol. 217:618–644; Cline, 1985, Pharmac. Ther. 29:69–92) and may be used to construct the recombinant hematopoietic cells for purposes of gene therapy. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, recombinant hematopoietic cells are administered intravenously. The amount of cells envisioned for use depends on the desired effect, patient state etc. and can be determined by one skilled in the art.

6.2. Preparation of Hematopoietic Cells in Vitro

Sources of hematopoietic stem and progenitor cells, which cells can be induced to proliferate according to one embodiment of the present invention, include but are not limited to bone marrow, fetal and neonatal blood (preferably from the umbilical cord and/or placenta), fetal liver, adult peripheral blood, neonatal thymus, and neonatal spleen. The foregoing list of sources is deemed to include cell samples (e.g., cryopreserved cells, cell lines, long-term cell cultures) derived therefrom. The source is mammalian, e.g., mouse, cow, horse, primate, monkey, and is most preferably human.

Techniques for obtaining such stem and progenitor cells are well known in the art. For example, in one particular embodiment, human bone marrow cells can be obtained from the posterior iliac crest by needle aspiration (see, e.g., Kodo et al., 1984, *J. Clin. Invest.* 73:1377–1384). Neonatal blood can be obtained at birth by direct drainage from the umbilical cord and/or by needle aspiration from the delivered placenta at the root and at distended veins (see U.S. Pat. Nos. 5,004,681 and 5,192,553). Fetal blood can be obtained, e.g., by taking it from the fetal circulation at the placental root with the use of a needle guided by ultrasound (Daffos et al., 1985, *Am. J. Obstet. Gynecol.* 153:655–660; Daffos et al., 1983, *Am. J. Obstet. Gynecol.* 146:985), by placentocentesis (Valenti, 1973, *Am. J. Obstet. Gynecol.* 115:851; Cao et al., 1982, *J. Med. Genet.* 19:81), by fetoscopy (Rodeck, C. H., 1984, in *Prenatal Diagnosis*, Rodeck, C. H. and Nicolaides, K. H., eds., Royal College of Obstetricians and Gynaecologists, London), etc.

The method of the invention which comprises contacting hematopoietic stem and/or progenitor cells (or other hematopoietic cells) with a Therapeutic of the invention, can be carried out on unseparated, partially separated, or purified cell populations, before and/or after cryopreservation (and thawing) or in vitro culturing of such cell populations, before and/or after introduction of a recombinant gene, and any other desired manipulations of the cells. In a preferred aspect, samples (e.g. bone marrow or adult blood or neonatal blood) can be subjected to physical and/or immunological cell separation procedures so as to enrich for hematopoietic stem and progenitor cells (e.g., prior to culturing in the presence of a Therapeutic of the invention to induce proliferation of the cells).

Various procedures are known in the art and can be used to enrich for stem and progenitor cells. These include but are not limited to equilibrium density centrifugation, velocity sedimentation at unit gravity, immune rosetting and immune adherence, counterflow centrifugal elutriation, T lymphocyte depletion, and fluorescence-activated cell sorting, alone or in combination. Procedures have been reported for the isolation of very highly enriched populations of stem/progenitor cells. U.S. Pat. No. 5,061,620 dated Oct. 29, 1991 discloses a method for isolation of human hematopoietic stem cells. Murine CFU-S have been purified by several groups using slightly different procedures (Visser et al., 1984, *J. Exp. Med.* 59:1576; Nijhof et al., 1984, *Exp. Cell Res.* 155:583; Bauman et al., 1986, *J. Cell. Physiol.* 128:133; Lord and Spooncer, 1986, *Lymphokine Res.* 5:59). Studies using human (Emerson et al., 1985, *J. Clin. Invest.* 76:1286) or murine (Nicola et al., 1981, *Blood* 58:376) fetal liver cells have yielded highly enriched progenitor cells with up to 90% of them being colony forming cells for multi-, erythroid-, and granulocyte-macrophage lineages. CFU-E have also been very highly enriched (Nijhof et al., 1983, *J. Cell Biol.* 96:386). Purification of adult mouse marrow CFU-GM with cloning efficiencies of up to 99% in semi-solid medium has been accomplished by pretreatment of mice three days prior to sacrifice with cyclophosphamide, density separation of cells on Ficoll-Hypaque, and counterflow centrifugal elutriation (Williams et al., 1987, *Exp. Hematol.* 15:243). The resulting fraction of cells contained no detectable CFU-GEMM, BFU-E or CFU-MK, but up to 10% of the cells formed CFU-S measured at day 12. These procedures, or modifications thereof, can be used.

Human stem and progenitor cells are present in the non-adherent, low density, T-lymphocyte-depleted fraction of bone marrow, spleen, and adult and cord blood cells. Low density (density less than 1.077 gm/cm$^3$) cells can be separated by use of Ficoll-Hypaque (Pharmacia Fine Chemicals, Piscataway, N.J.) or Percol (Broxmeyer, H. E., 1982, *J. Clin. Invest.* 69:632–642). In this procedure, the mature cells of the granulocytic series, which are not needed for transplantation, are removed in the dense fraction which goes to the bottom of the tube. An adherence/nonadherence separation protocol can also be used for enrichment of hematopoietic stem and progenitor cells.

It is also possible to use cell separation procedures that entail immunological recognition of cells. Stem and progenitor cells can be isolated by positive or negative selection using antibodies that recognize antigenic determinants on the surface of cells. One means is to separate the cells by using monoclonal antibodies which recognize cell surface determinants on these cells, in conjunction with separation procedures such as fluorescence-activated cell sorting or panning (Broxmeyer et al., 1984, *J. Clin. Invest.* 73:939–953). Human hematopoietic stem and progenitor cells contain antigenic determinants that are not present on all other cells, which can be used in antibody selection protocols for enrichment purposes; such antigens include but are not limited to those described infra.

Within the human system, several antigens have been found on stem/progenitor cells. The first antigenic system studied intensively was that of the MHC class II antigens, especially HLA-DR. This antigen has been found on CFU-GEMM, BFU-E, and CFU-GM (Lu et al., 1983, *Blood* 61:250; Winchester et al., 1977, *Proc. Natl. Acad. Sci. U.S.A.* 74:4012; Busch et al., 1987, *Blut* 54:179). Several investigators have suggested that HLA-DR are not found, or are present at a low density on cells earlier than CFU-GEMM (Moore et al., 1980, *Blood* 55:682; Keating et al., 1984, *Blood* 64:1159).

Groups of antibodies have been used to distinguish different progenitors of the granulocyte-macrophage lineage (Ferrero et al., 1983, *Proc. Natl. Acad. Sci. U.S.A.* 80:4114). Type 1 CFU-GM contribute all of the peripheral blood CFU-GM, as well as a small number of bone marrow CFU-GM. They express surface antigens recognized by S3-13 and S17-25 antibodies, but not by R1B19 and WGHS-29-1 antibodies. Type 2 CFU-GM are present only in the marrow and react with S3-13, R1B19, and WGHS-29-1. Culture of type 1 CFU-GM in liquid culture generates type 2 CFU-GM. These antibodies have also been used to characterize CFU-GM from patients with chronic myeloproliferative disorders (Robak et al., 1985, *Leukemia Res.* 9:1023; Ferrero et al., 1986, *Cancer Res.* 46:975).

Other antigens on human stem/progenitor cells include those reactive with the My10 (Leary et al., 1987, *Blood* 69:953; Strauss et al., 1986, *Exp. Hematol.* 14:879), 3C5 (Katz et al., 1985, *Leukemia Res.* 9:191; Katz et al., 1986, *Leukemia Res.* 10:961), RFB-1 (Bodger et al., 1983, *Blood* 61:1006), 12-8 (Andrews et al., 1986, *Blood* 67:842), and L4F3 (Andrews et al., 1986, *Blood* 68:1030) antibodies. The antigen recognized by L4F3 is on CFU-GM, CFU-MK, BFU-E, and CFU-GEMM, but is apparently absent from cells which generate these progenitors in suspension culture (id.). The antigen recognized by the My10 antibody is CD34 (Civin et al., U.S. Pat. No. 4,714,680 dated Dec. 22, 1987.) Two subsets of pluripotent hematopoietic stem cells have been reported, a CD34$^+$ HLA-DR$^+$ CD38$^-$ subset and a more primitive CD34+HLA-DR$^-$ CD38$^-$ subset, with a gradual increase in CD38 expression as the hematopoietic cells proceed toward a more differentiated state (Huang and Terstappen, 1992, *Nature* 360:745–749; Terstappen et al., 1992, *Leukemia* 6:993–1000). The antigen recognized by another antibody, My11 is expressed on CFU-GM, but not on BFU-E or CFU-GEMM (Strauss et al,., 1986, *Exp. Hematol.* 14:935). Receptors for various lectins are also expressed on stem/progenitor cells (Nicola et al., 1980, *J. Cell Physiol.* 103:217; Reisner et al., .1982, *Blood* 59:360; Reisner et al., 1978, *Proc. Natl. Acad, Sci. U.S.A.* 75:2933; Aizawa and Tavassoli, 1986, *Int. J. Cell Cloning* 4:464).

To expand the numbers of the hematopoietic stem and/or progenitor cells, the hematopoietic stem and/or progenitor cells (or precursor cells thereof) are exposed to or contacted with a composition comprising a Therapeutic of the invention for a sufficient time period, i.e., until the desired number of cells is obtained and the time period should be for as long as it is desired to keep cells self-renewing. Preferably, the cells are contacted with the Therapeutic, for example but not limited to, 200 IU/ml hCG (e.g., hCG APL) or β-hCG preparation or 100 μg/ml β-hCG peptide, preferably a β-hCG peptide having the amino acid sequence of amino acid numbers 45–57 or 109–119 (SEQ ID NOS:6 or 7, respectively), or circularized peptide of amino acid numbers 44–57 (SEQ ID NO:12) with cysteine substituted for valine at position 44, or a branched peptide of amino acid numbers 45–57 (SEQ ID NO:6) with diaminobutyric acid substituted for the amino acids at positions 47 and 51 with proline peptide bonded to the diaminobutyric acid residues, or a circularized branched peptide of amino acids 44–57 (SEQ ID NO:12) with cysteine substituted for valine at position 44 and with diaminobutyric acid substituted for the amino acids at positions 47 and 51 with proline peptide bonded to the diaminobutyric acid residues, where all amino acid numbers are of the β-hCG sequence depicted in FIG. 4 (a portion of SEQ ID NO:2), while under appropriate culture conditions, for a time period in the range of 1–21 or, more preferably, 7–21 days.

The composition comprising the Therapeutic of the invention, to which the stem and progenitor cells are exposed according to the invention, optionally also. contains other growth factors and/or cytokines or cell culture materials, including but not limited to erythropoietin (Epo), Steel factor (SLF), IL-1, IL-3, IL-4, IL-6, IL-11, G-CSF, GM-CSF, FBS, adult PB plasma, alone or in combination. Preferably, factors are present that cause proliferation or, less preferably, differentiation of cells that are CFU-GEMM or earlier cells, e.g., IL-3, GM-CSF.

Contacting of the stem and progenitor cells with the Therapeutic preferably occurs during cell culture and thus, the Therapeutic is preferably added to the cell culture medium being used to culture the hematopoietic stem and/or progenitor cells. Such culturing can be by any method known in the art, including, but not limited to, cells grown in culture dishes, test tubes, roller bottles, bioreactors (perfusion system machines wherein cells are grown on a surface with continual perfusion by medium; e.g., as sold by Aastrom Biosciences, Inc., Ann Arbor, Mich.), etc. Various protocols have been described for the growth in vitro of cord blood or bone marrow cells, and it is envisioned that such procedures, or modifications thereof, may be employed (see, e.g. Smith, S. and Broxmeyer, H. E., 1986, *Br. J. Haematol.* 63:29–34; Dexter et al., 1977, *J. Cell. Physiol.* 91:335; Witlock and Witte, 1982, *Proc. Natl. Acad. Sci. U.S.A.* 79:3608–3612). The cell culture medium is supplemented to contain an effective concentration of the Therapeutic, for example but not limited to, 200 I.U. hCG (APL) or β-hCG preparation or 100 μg/ml of a β-hCG peptide.

Progeny cells of hematopoietic stem and progenitor cells of can be generated in vitro; the differentiated progeny cells thus generated can be therapeutically useful. For example, in one embodiment of this aspect of the invention, hematopoietic stem cells and/or CFU-GEMM progenitor cells, can be induced to differentiate into platelets. Such platelets can be used, for example, for infusion into a patient with thrombocytopenia, such as, but not limited to, the ITP associated with HIV infection. In another embodiment, granulocytes can be generated in vitro prior to infusion into a patient. One or more of the hematopoietic progeny cells can be generated in vitro, allowing for the in vitro production of blood components. In one embodiment, the generation of differentiated blood components is accompanied by expansion of the hematopoietic stem and progenitor cell pool in order to allow for production of a greater quantity of differentiated cells. Various growth factors can be used to promote expansion and/or differentiation of hematopoietic stem and progenitor cells, such as cytokines (growth factors) including, but not limited to, G-CSF, CSF-1, IL-3, IL-5, tumor necrosis factor-β, and α-interferon. The blood components which are thus produced have uses which are not limited to therapeutic uses in vivo. For example, such progeny cells can be used in vitro, e.g., for the production and isolation of hematopoietic cell products such as growth factors, antibodies, etc.

A specific embodiment of the invention relates to a method of increasing the amount of hematopoietic cells, which method comprises contacting in vitro a non-terminally differentiated hematopoietic cell with a composition comprising an amount of a Therapeutic of the invention effective to increase proliferation of the cell, under conditions suitable and for a time period sufficient to increase the numbers of said hematopoietic cell. For example, hematopoietic cell numbers can be increased by contacting a non-terminally differentiated hematopoietic cell (e.g., a cell isolated from bone marrow or blood, adult or fetal or umbilical cord blood) with a composition comprising 200 IU/ml hCG (e.g., hCG APL) or β-hCG preparation or 100 μg/ml β-hCG peptide, preferably a β-hCG peptide having the amino acid sequence of amino acid numbers 45–57 or 109–119 (SEQ ID NOS:6 or 7, respectively), or circularized peptide of amino acid numbers 44–57 (SEQ ID NO:12) with cysteine substituted for valine at position 44, or a branched peptide of amino acid numbers 45–57 (SEQ ID NO:6) with diaminobutyric acid substituted for the amino acids at positions 47 and 51 and proline residues peptide bonded to the diaminobutyric acid residues, or a circularized branched peptide of amino acids 44–57 (SEQ ID NO:12) with cysteine substituted for valine at position 44 and with diaminobutyric acid substituted for the amino acids at positions 47 and 51 with a proline residue peptide bonded to the diaminobutyric acid residues, where all amino acid numbers are of the β-hCG sequence depicted in FIG. 4 (a portion of SEQ ID NO:2), and culturing the cell for at least ten days.

6.3. hCG, β-hCG and β-hCG Peptides and Derivatives Thereof

Native preparations of hCG and β-hCG can be obtained from a variety of sources. Both hCG and β-hCG are commercially available (e.g., Sigma Chemical Company) and hCG is commercially available in a form suitable for therapeutic use in humans (e.g., from Fujisawa, Wyeth-Ayerst Laboratories (APL™), Organon, Inc. (Pregnyl™) and Serono Laboratories, Inc. (Profasi™)). The inventors have discovered that different sources of hCG and β-hCG have variable effects on hematopoiesis in vitro and in vivo; thus, one aspect of the invention relates to assaying preparations comprising hCG, β-hCG, or fragments or derivatives thereof, for efficacy in inducing proliferation of hematopoietic cells. The therapeutic effectiveness of hCG preparations can be tested by the in vitro or in vivo assays described in Section 5.4 infra or by any method known in the art. It is preferable to test the hCG preparation in an in vitro assay, e.g., for colony formation from bone marrow or human cord blood cells, or in an animal model, such as in monkeys infected with SIV, before assaying the preparation in humans.

In a specific embodiment, a preparation comprising hCG is used that contains not only the hCG heterodimer but also peptide fragments thereof, e.g., β chain peptides.

hCG and β-hCG can also be purified, or preferably partially purified, from any source known to contain hCG, e.g., urine from pregnant women, using conventional techniques well-known in the art, such as affinity chromatography. For example, antibodies prepared against hCG or β-hCG can be used to prepare an affinity chromatography column which can be used to purify the proteins by well-known techniques (see, e.g., Hudson & May, 1986, *Practical Immunology*, Blackwell Scientific Publications, Oxford, United Kingdom).

The β-hCG-related proteins are preferably prepared by any chemical or enzymatic synthesis method well-known in the art, as described infra.

In a preferred embodiment of the invention, proteins (e.g., peptides), the amino acid sequence of which consists of a portion effective to increase the production of one or more hematopoietic cell types of the β-hCG sequence (β-hCG peptides) are used to treat or prevent hematopoietic deficiencies. In various specific embodiments, the portions of the β-hCG sequence are at least 3, 5, 10, 20, or 30 amino acids. These proteins are preferably β-hCG peptides, or nucleic acids encoding β-hCG peptides, from amino acids 41–54, 45–54, 47–53 and 45–57 (SEQ ID NOS:3–6, respectively) of FIG. 4 (a portion of SEQ ID NO:2). In other embodiments, β-hCG peptides of 41–53, 42–53, 43–53, 44–53, 44–57, 45–53, 46–53, 45–54, 45–55, 45–56, 45–58, 47–54, 47–55, 47–56, 47–58, 48–145, 58–145, 109–119 and 109–145 (SEQ ID NOS:8–24, 7 or 25, respectively) of FIG. 4 (a portion of SEQ ID NO:2) are used to treat or prevent hematopoietic deficiencies. In another embodiment, a protein is used that (a) comprises a portion of the amino acid sequence consisting of β-hCG, a peptide having an amino acid sequence consisting of said portion being effective to increase production of one or more hematopoietic cell types; and (b) lacks β-hCG amino acids contiguous to said portion. In another embodiment, a protein is used that (a) comprises a β-hCG amino acid sequence consisting of amino acid numbers 41–54, 45–54, 47–53, 45–57, 45–58, 41–53, 42–53, 43–53, 44–53, 44–57, 45–53, 46–53, 45–54, 45–55, 45–56, 47–54, 47–55, 47–56, 47–58, 48–145, 58–145, 109–119 or 109–145 (SEQ ID NOS:3–6, 18, 8–17, 19–24, 7 and 25, respectively) as depicted in FIG. 4 (a portion of SEQ ID NO:2) and (b) lacks β-hCG amino acids contiguous to said sequence. Other β-hCG peptides, and nucleic acids encoding these peptides, may have utility in the therapeutic methods of the invention. The utility of β-hCG peptides may be determined by the in vitro and in vivo assays described in Section 5.4 infra or by any other method known in the art.

In specific embodiments, peptides of less than 50 or less than 25, amino acids are provided.

The invention also relates to derivatives modifications and analogs of β-hCG peptides. One embodiment of the invention provides a purified derivative of a protein effective to increase the production of one or more hematopoietic cell types, which protein contains an amino acid sequence of a portion effective to increase the production of one or more hematopoietic cell types of β-hCG. Another embodiment of the invention provides a purified derivative of a protein effective to increase the production of one or more hematopoietic cell types, the amino acid sequence of which protein is selected from the group consisting of amino acid numbers 41–54, 45–54, 47–53, 45–57, 45–58, 41–53, 42–53, 43–53, 44–53, 44–57, 45–53, 46–53, 45–54, 45–55, 45–56, 47–54, 47–55, 47–56, 47–58, 48–145, 58–145, 109–119 or 109–145 (SEQ ID NOS:3–6, 18, 8–17, 19–24, 7 and 25, respectively) as depicted in FIG. 4 (a portion of SEQ ID NO:2). In another embodiment, β-hCG peptide derivatives can be made by altering the β-hCG peptide sequence by substitutions, additions or deletions that provide for therapeutically effective molecules. Thus, the β-hCG peptide derivatives include peptides containing, as a primary amino acid sequence, all or part of the particular β-hCG peptide sequence including altered sequences in which functionally equivalent amino acid residues are substituted for residues within the sequence resulting in a peptide which is functionally active. For example, one or more amino acid residues within the sequence can be substituted by another amino acid of a similar polarity which acts as a functional equivalent, resulting in a silent alteration. Conservative substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such β-hCG peptide derivatives can be made either by chemical peptide synthesis or by recombinant production from a nucleic acid encoding the β-hCG peptide which nucleic acid has been mutated. Any technique for mutagenesis known in the art can be used, including but not limited to, chemical mutagenesis, in vitro site-directed mutagenesis (Hutchinson, C., et al., 1978, *J. Biol. Chem* 253:6551), use of TAB® linkers (Pharmacia), etc.

In addition, β-hCG peptides and analogs and derivatives of β-hCG peptides can be chemically synthesized. See, e.g., Merrifield, 1963, *J. Amer. Chem. Soc.* 85:2149–2156.) For example, peptides can be synthesized by solid phase techniques, cleaved from the resin, and purified by preparative high performance liquid chromatography (e.g., see Creighton, 1983, Proteins, Structures and Molecular Principles, W.H. Freeman and Co., N.Y., pp. 50–60). β-hCG peptides can also be synthesized by use of a peptide synthesizer. The composition of the synthetic peptides may be confirmed by amino acid analysis or sequencing (e.g., the Edman degradation procedure; see Creighton, 1983, Proteins, Structures and Molecular Principles, W.H. Freeman and Co., N.Y., pp. 34–49). Furthermore, if desired, non-classical amino acids or chemical amino acid analogs can be introduced as a substitution or addition into the β-hCG peptide. Non-classical amino acids include but are not-limited to the D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

By way of example but not by way of limitation, peptides of the invention can be chemically synthesized and purified as follows: Peptides can be synthesized by employing the N-α-9-fluorenylmethyloxycarbonyl or Fmoc solid phase peptide synthesis chemistry using a Rainin Symphony Multiplex Peptide Synthesizer. The standard cycle used for coupling of an amino acid to the peptide-resin growing chain generally includes: (1) washing the peptide-resin three times for 30 seconds with N,N-dimethylformamide (DMF); (2) removing the Fmoc protective group on the amino terminus by deprotection to with 20% piperdine in DMF by two washes for 15 minutes each, during which process mixing is effected by bubbling nitrogen through the reaction vessel for one second every 10 seconds to prevent peptide-resin settling; (3) washing the peptide-resin three times for 30 seconds with DMF; (4) coupling the amino acid to the peptide resin by addition of equal volumes of a 250 mM solution of the Fmoc derivative of the appropriate amino acid and an activator mix consisting or 400 mM N-methylmorpholine and 250 mM (2-(1H-benzotriazol-1-4))-1,1,3,3-tetramethyluronium hexafluorophosphate (HBTU) in DMF; (5) allowing the solution to mix for 45 minutes; and (6) washing the peptide-resin three times for 30 seconds of DMF. This cycle can be repeated as necessary with the appropriate amino acids in sequence to produce the desired peptide. Exceptions to this cycle program are amino acid couplings predicted to be difficult by nature of their hydrophobicity or predicted inclusion within a helical formation during synthesis. For these situations, the above cycle can be modified by repeating step 4 a second time immediately upon completion of the first 45 minute coupling step to "double couple" the amino acid of interest. Additionally, in the first coupling step in peptide synthesis, the resin can be allowed to swell for more efficient coupling by increasing the time of mixing in the initial DMF washes to three 15 minute washes rather than three 30 second washes. After peptide synthesis, the peptide can be cleaved from the resin as follows: (1) washing the peptide-resin three times for 30 seconds with DMF; (2) removing the Fmoc protective group on the amino terminus by washing two times for 15 minutes it 20% piperdine in DMF; (3) washing the peptide-resin three times for 30 seconds with DMF; and (4) mixing a cleavage cocktail consisting of 95% trifluoroacetic acid (TFA), 2.4% water, 2.4% phenol, and 0.2% triisopropysilane with the peptide-resin for two hours, then filtering the peptide in the cleavage cocktail away from the resin, and precipitating the peptide out of solution by addition of two volumes of ethyl ether. Specifically, to isolate the peptide, the ether-peptide solution can be allowed to sit at –20° C. for 20 minutes, then centrifuged at 6,000×G for 5 minutes to pellet the peptide, and the peptide can be washed three times with ethyl ether to remove residual cleavage cocktail ingredients. The final peptide product can be purified by reversed phase high pressure liquid chromatography (RP-HPLC) with the primary solvent consisting of 0.1% TFA and the eluting buffer consisting of 80% acetonitrile and 0.1% TFA. The purified peptide can then be lyophilized to a powder.

In a preferred embodiment, the invention provides a peptide with branched amino acids (branched peptide), preferably a branched peptide of amino acids 45–57 (SEQ ID NO:6) with branches occurring at positions 47 and 51, respectively, instead of the Gly and Ala residues normally present. Most preferably, diaminobutyric acid is substituted for the gly and ala residues at positions 47 and 51, respectively, and proline bonded to both diaminobutyric acid residues (45–57 branched) as shown in FIG. 5A.

In other specific embodiments, branched versions of the β-hCG peptides listed hereinabove are provided, eg., by substituting one or more amino acids within the β-hCG sequence with an amino acid or amino acid analog with a free side chain capable of forming a peptide bond with cone or more amino acids (and thus capable of forming a "branch").

Branched peptides may be prepared by any method known in the art for covalently linking any naturally occurring or synthetic amino acid to any naturally occurring or synthetic amino acid in a peptide chain which has a side chain group able to react with the amino or carboxyl group on the amino acids so as to become covalently attached to the peptide chain. In particular, amino acids with a free amino side chain group, such as, but not limited to, diaminobutyric acid, lysine, arginine, ornithine, diaminopropionic acid and citrulline, can be incorporated into a peptide so that an amino acid can form a branch therewith, for example, by forming a peptide bond to the free amino side group, from that residue. Alternatively, amino acids with a free carboxyl side chain group, such as, but not limited to, glutamic acid, aspartic acid and homocitrulline, can be incorporated into the peptide so that an amino acid can form a branch therewith, for example, by forming a peptide bond to the free carboxyl side group, from that residue. The amino acid forming the branch can be linked to a side chain group of an amino acid in the peptide chain by any type of covalent bond, including, but not limited to, peptide bonds, ester bonds and disulfide bonds. In a specific embodiment, amino acids, such as those described above, that are capable of forming a branch point, are substituted for β-hCG residues within a peptide having a β-hCG sequence.

Branched peptides can be prepared by any method known in the art. For example, but not by way of limitation, branched peptides can be prepared as follows: (1) the amino acid to be branched from the main peptide chain can be purchased as an N-α-tert-butyloxycarbonyl (Boc) protected amino acid pentafluorophenyl (Opfp) ester and the residue within the main chain to which this branched amino acid will be attached can be an N-Fmoc-α-γ-diaminobutyric acid; (2) the coupling of the Boc protected amino acid to diaminobutyric acid can be achieved by adding 5 grams of each precursor to a flask containing 150 ml DMF, along with 2.25 ml pyridine and 50 mg dimethylaminopyridine and allowing the solution to mix for 24 hours; (3) the peptide can then be extracted from the 150 ml coupling reaction by mixing the reaction with 400 ml dichlormethane (DCM) and 200 ml 0.12N HCl in a 1 liter separatory funnel, and allowing the phases to separate, saving the bottom aqueous layer and re-extracting the top layer two more times with 200 ml 0.12N HCl; (4) the solution containing the peptide can be dehydrated by adding 2–5 grams magnesium sulfate, filtering out the magnesium sulfate, and evaporating the remaining solution to a volume of about 2–5 ml; (5) the dipeptide can then be precipitated by addition of ethyl acetate and then 2 volumes of hexanes and then collected by filtration and washed two times with cold hexanes; and (6) the resulting filtrate can be lyophilized to achieve a light powder form of the desired dipeptide. Branched peptides prepared by this method will have a substitution of diaminobutyric acid at the amino acid position which is branched. Branched peptides containing an amino acid or amino acid analog substitution other than diaminobutyric acid can be prepared analogously to the procedure described above, using the N-F-moc coupled form of the amino acid or amino acid analog.

Figure 5B:
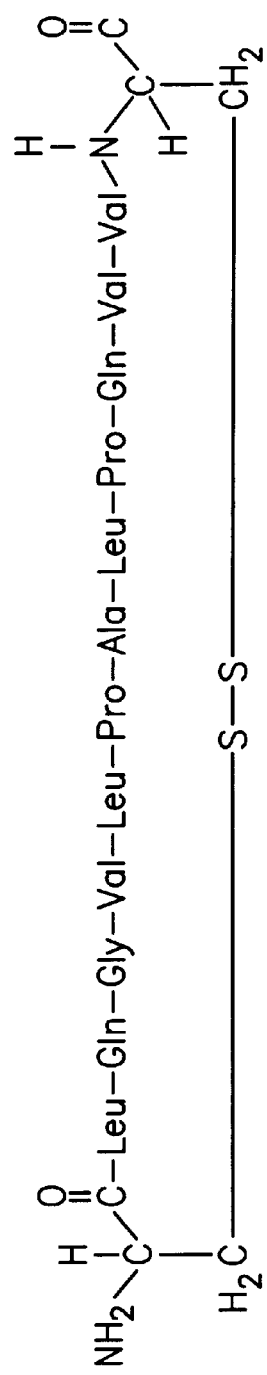

In a preferred embodiment, the peptide is a cyclic peptide, preferably a cyclic peptide of β-hCG a 44–57 (SEQ ID NO:26) with cysteine substituted for valine at position 44 and circularized via a disulfide bond between the cysteine residues at positions 44 and 57 (C[V44C] 45–57) (FIG. 5B). In another preferred embodiment, the peptide is a cyclic branched peptide of β-hCG amino acids 44–57 (SEQ ID NO:12) with cysteine substituted for valine at position 44 and circularized via a disulfide bond between the cysteine residues at positions 44 and 57 and positions 47 and 51 substituted with a diaminobutyric acid residue on which a proline is peptide bonded to its free amino sidechain.

Cyclization can be, for example, but not by way of limitation, via a disulfide bond between two cysteine residues or via an amide linkage. For example, but not by way of limitation, disulfide bridge formation can be achieved by (1) dissolving the purified peptide at a concentration of between 0.1–0.5 mg/ml in 0.01 M ammonium acetate, pH 7.5; (2) adding to the dissolved peptide 0.01M potassium ferricyanide dropwise until the solution appears pale yellow in color and allowing this solution to mix for 24 hours; (3) concentrating the cyclized peptide to 5–10 ml of solution, repurifying the peptide by reverse phase-high pressure liquid chromatography (RP-HPLC) and finally lyophilizing the peptide. In a specific embodiment, in which the peptide does not contain two appropriately situated cysteine residues, cysteine residues can be introduced at the amino-terminus and/or carboxy-terminus and/or internally such that the peptide to be cyclized contains two cysteine residues spaced such that the residues can form a disulfide bridge. Alternatively, a cyclic peptide can be obtained by generating an amide linkage using, for example but not limited to, the following protocol: An allyl protected amino acid, such as aspartate, glutamate, asparagine or glutamine, can be incorporated into the peptide as the first amino acid, and then the remaining amino acids are coupled on. The allyl protective group can be removed by a two hour mixing of the peptide-resin with a solution of tetrakistriphenylphophine palladium (0) in a solution of chloroform containing 5% acetic acid and 2.5% N-methylmorpholine. The peptide resin can be washed three times with 0.5% N,N-diisopropylethylamine (DIEA) and 0.5% sodium diethyldithiocabamate in DMF. The amino terminal Fmoc group on the peptide chain can be removed by two incubations for 15 minutes each in 20% piperdine in DMF, and washed three times with DMF for 30 seconds each. The activator mix, N-methylmorpholine and HBTU in DMF, can be brought onto the column and allowed to couple the free amino terminal end to the carboxyl group generated by removal of the allyl group to cyclize the peptide. The peptide can cleaved from the resin as described in the general description of chemical peptide synthesis above and the peptide purified by reverse phase-high pressure liquid chromatography (RP-HPLC). In a specific embodiment, in which the peptide to be cyclized does not contain an allyl protected amino acid, an allyl protected amino acid can be introduced into the sequence of the peptide, at the amino-terminus, carboxy-terminus or internally, such that the peptide can be cyclized.

β-hCG peptides can also be obtained by recombinant expression techniques. (See, e.g., Sambrook et al., 1989, Molecular Cloning, A Laboratory Manual, Cold Spring Harbor Laboratory, 2d Ed., Cold Spring Harbor, N.Y., Glover, D. M. (ed.), 1985, DNA Cloning: A Practical Approach, MRL Press, Ltd., Oxford, U.K., Vol. I, II). The nucleic acid sequence encoding hCG has been cloned and the sequence determined (see FIG. 4 and Xia, H., 1993, *J. Molecular Endocrinology* Jun. 10; 1993:337–343; Sherman, G. B., 1992, *J. Molecular Endocrinology*, Jun. 6, 1992:951–959; Gieseman, L. K. (ed.), 1991, *Basic and Chemical Endocrinology*, pp. 543–567; Ward et al., 1991, in *Reproduction in Domestic Animals*, 4th ed., P. T. Coppos, ed., pp. 25–80, Academic Press, New York) and can be isolated using well-known techniques in the art, such as screening a library, chemical synthesis, or polymerase chain reaction (PCR).

To recombinantly produce a β-hCG peptide, a nucleic acid sequence encoding the β-hCG peptide is operatively linked to a promoter such that the β-hCG peptide is produced from said sequence. For example, a vector can be introduced into a cell, within which cell the vector or a portion thereof is expressed, producing the β-hCG peptide. In a preferred embodiment, the nucleic acid is DNA if the source of RNA polymerase is DNA-directed RNA polymerase, but the nucleic acid may also be RNA if the source of polymerase is RNA-directed RNA polymerase or if reverse transcriptase is present in the cell or provided to produce DNA from the RNA. Such a vector can remain episomal or, become chromosomally integrated, as long as it can be transcribed to produce the desired RNA. Such vectors can be constructed by recombinant DNA technology methods standard in the art. Vectors can be plasmid, viral, or others known in the art, used for replication and expression in bacterial or mammalian cells. Expression of the sequence encoding the β-hCG peptide can be by any promoter known in the art to act in bacterial or mammalian cells. Such promoters can be inducible or constitutive. Such promoters include, but are not limited to: the SV40 early promoter region (Bernoist and Chambon, 1981, *Nature* 290:304–310), the promoter contained in the 3 long terminal repeat of Rous sarcoma virus (Yamamoto et al., 1980, *Cell* 22:787–797), the HSV-1 (herpes simplex virus-1) thymidine kinase promoter (Wagner et al., 1981, *Proc. Natl. Acad. Sci. USA* 78:1441–1445), the regulatory sequences of the metallothionein gene (Brinster et al., 1982, *Nature* 296:39–42), etc., as well as the following animal transcriptional control regions, which exhibit tissue specificity and have been utilized in transgenic animals: elastase I gene control region which is active in pancreatic acinar cells (Swift et al., 1984, *Cell* 38:639–646; Ornitz et al., 1986, *Cold Spring Harbor Symp. Quant. Biol.* 50:399–409; MacDonald, 1987, *Hepatology* 7:425–515); insulin gene control region which is active in pancreatic beta cells (Hanahan, 1985, *Nature* 315:115–122), immunoglobulin gene control region which is active in lymphoid cells (Grosschedl et al., 1984, *Cell* 38:647–658; Adames et al., 1985, *Nature* 318:533–538; Alexander et al., 1987, *Mol. Cell. Biol.* 7:1436–1444), mouse mammary tumor virus control region which is active in testicular, breast, lymphoid and mast cells (Leder et al., 1986, *Cell* 45:485–495), albumin gene control region which is active in liver (Pinkert et al., 1987, *Genes and Devel.* 1:268–276), alpha-fetoprotein gene control region which is active in liver (Krumlauf et al., 1985, *Mol. Cell. Biol.* 5:1639–1648; Hammer et al., 1987, *Science* 235:53–58), alpha 1-antitrypsin gene control region which is active in the liver (Kelsey et al., 1987, *Genes and Devel.* 1:161–171), beta-globin gene control region which is active in erythroid cells (Mogram et al., 1985, *Nature* 315:338–340; Kollias et al., 1986, *Cell* 46, 89–94), myelin basic protein gene control region which is active in oligodendrocyte cells in the brain (Readhead et al., 1987, *Cell* 48:733–712), myosin light chain-2 gene control region which is active in skeletal muscle (Sani, 1985, *Nature* 314:283–286), and gonadotropin releasing hormone gene control region which is active in the hypothalamus (Mason et al., 1986, *Science* 234:1372–1378). The promoter element which is operatively linked to the nucleic acid encoding the β-hCG peptide can also be a bacteriophage promoter with the source of the bacteriophage RNA polymerase expressed from a gene for the RNA polymerase on a separate plasmid, e.g., under the control of an inducible promoter, for example, a nucleic acid encoding the β-hCG peptide operatively linked to the T7 RNA polymerase promoter with a separate plasmid encoding the T7 RNA polymerase.

In a less preferred embodiment, peptides can be obtained by proteolysis of hCG followed by purification using standard techniques such as chromatography (e.g., HPLC), electrophoresis, etc.

Also included within the scope of the invention are β-hCG peptide derivatives which are differentially modified during or after synthesis, e.g., by benzylation, glycosylation, acetylation, phosphorylation, amidation, pegylation, derivatization by known protecting/blocking groups, proteolytic cleavage, linkage to an antibody molecule or other cellular ligand, etc. In specific embodiments, the peptides are acetylated at the N-terminus and/or amidated at the C-terminus. Any of numerous chemical modifications may be carried out by known techniques, including but not limited to acetylation, formylation, oxidation, reduction; metabolic synthesis in the presence of tunicamycin; etc.

In another embodiment, the β-hCG peptide derivative is a chimeric, or fusion, protein comprising a functional β-hCG peptide joined at its amino- or carboxy-terminus via a peptide bond to an amino acid sequence of a different protein. In one embodiment, such a chimeric protein is produced by recombinant expression of a nucleic acid encoding the protein (comprising a β-hCG-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

6.4. Assays for Induction of Hematopoirtic Cell Proliferation

The Therapeutics of the invention are preferably tested in vitro, and then in vivo for the desired therapeutic or prophylactic activity, prior to use in humans. Any in vitro or in vivo assay known in the art to measure a pro-hematopoietic effect, i.e. the ability to induce hematopoietic cell proliferation in vitro or production of one or more hematopoietic cell types in vivo, such as those described in Section 6 infra, can be used to test the efficacy of a Therapeutic of the invention.

A specific embodiment provides a method for screening a preparation comprising hCG or an hCG α chain or hCG β chain or a derivative of hCG or of said alpha or beta chain, for pro-hematopoietic activity comprising assaying said preparation for the ability to induce an increase in hematopoietic cell numbers. In one embodiment, the preparation is screened by a method comprising measuring the number of colonies formed from hematopoietic stem or progenitor cells, which cells have been contacted with the preparation; and comparing the number of colonies formed from the cells contacted with the preparation with the number of colonies formed from cells not so contacted with the preparation, wherein a higher number of colonies formed from said contacted cells indicates that the preparation has pro-hematopoietic activity. In another embodiment, the preparation is screened by a method comprising measuring the number of CD4$^+$ T cells in an SIV infected monkey, which monkey has been exposed to the preparation; and comparing the number of CD4$^+$ T cells in the monkey which has been exposed to the preparation with the number of CD4$^+$ T cells in a monkey not so exposed, wherein a higher number of CD4$^+$ T cells in said exposed monkey indicates that the preparation has pro-hematopoietic activity.

Specifically, to assay a Therapeutic in vitro, one could examine the effect of the Therapeutic on proliferation of hematopoietic cells in vitro. For example, to assay colony-forming units (a progenitor cell), briefly, the hematopoietic cells are cultured for an appropriate amount of time, such as 5 to 20 days and preferably 10 days, in the presence of (or otherwise exposed to) the Therapeutic to be tested, and then colony assays are performed to determine the number of colonies formed in comparison to the number of colonies formed by cells cultured in the absence of the Therapeutic. For example, hematopoietic progenitor cells can be isolated from bone marrow or cord blood, seeded in methylcellulose in the presence of absence of the Therapeutic, and then colony numbers determined after 10 days of culture. An increase in colony numbers in cells contacted with the Therapeutic indicates that the Therapeutic has activity in inducing proliferation of hematopoietic cells. Thus, for example, depending on the progenitor cell desired to be assayed, CFU-GM, CFU-GEMM, etc., assays can be done.

Therapeutics can also be tested in vivo for activity in increasing the numbers of hematopoietic cells. Preferably, Therapeutics are tested in animal models of hematopoietic disorders before testing them in human patients. For example, but not by way of limitation, a Therapeutic can be tested in rhesus monkeys infected with SIV, particularly SIV$_{mac25}$, which induces a syndrome in monkeys similar to human AIDS (Kestler, H. et.al., 1990, *Science* 248:1109–1112), and which are deficient in CD4$^+$ T cells. The Therapeutic to be tested can be administered to the infected monkeys; then the blood or bone marrow of the infected monkeys can be examined for an increase in CD4$^+$ T cells or any other hematopoietic cell type for which the monkey is deficient. An increase in numbers of the hematopoietic cell demonstrates that the Therapeutic is useful for treating diseases and disorders associated with hematopoietic deficiencies. Any animal model of an anemia can be similarly used for testing.

Therapeutics can be tested in human patients, preferably after tests in vitro and/or in vivo in an animal model, with hematopoietic deficiencies, for example but not limited to, deficiencies associated with HIV infection such as anemia, neutropenia, thrombocytopenia, or CD4$^+$ T cell lymphocyte deficiency, for activity in increasing numbers of hematopoietic cells for which the patient is deficient. Briefly, the Therapeutic is administered, for example by intramuscular injection two to three times per week, to the patient suffering from the hematopoietic deficiency. The subject's blood or bone marrow is assayed before and after treatment with the Therapeutic for an increase in the hematopoietic cell numbers. Therapeutics which cause an increase in hematopoietic cell numbers are useful for treatment of diseases and disorders associated with hematopoietic deficiencies.

Assays for hematopoietic cell proliferation in the blood or bone marrow can be accomplished by any method well known in the art. For example, blood can be drawn and blood cell numbers can be determined by routine clinical laboratory tests for red blood cells, platelets, neutrophils, lymphocytes, etc. Additionally, colony assays on isolated bone marrow can be performed to assess increases in stem or progenitor cells. For example, bone marrow can be sampled and bone marrow cells evaluated for stem and progenitor cell colony formation. Briefly, cells are seeded in methylcellulose, cultured for 12 to 14 days, and then scored for colony formation where aggregates containing more than 50 cells are counted as a colony (see, e.g., Lunardi-Iskandar, Y. et al., 1995, Nature 375:64–68; Louache, R. et al., 1992, Blood 180:2991–2999; Lunardi-Iskandar, Y. et al., 1989, J. Clin. Invest. 83:610–615). Bone marrow progenitors which can be evaluated by this colony assay include, but are not limited to, CFU-Mix, BFU-e and CFU-GM. As an alternative to colony assays for detection and quantitation of stem and/or progenitor cells, immunological detection methods can be employed, based on the antigens expressed by the particular cell type (see, e.g., the relevant discussion in Section 5.2 hereinabove).

6.5. Therapeutic Compositions and Methods of Administration

The invention provides methods of treatment and prevention by administration to a subject of an effective amount of a Therapeutic of the invention. The subject is preferably an animal, including, but not limited to, animals such as cows, pigs, horses, chickens, cats, dogs, etc., and is preferably a mammal, and most preferably human. In a specific embodiment, the subject is a human not afflicted with a cancer which secretes hCG or hCG fragments and, more particularly, not afflicted with Kaposi's Sarcoma.

One embodiment of the invention provides for methods of administering a pharmaceutical composition which is comprised of a therapeutically effective amount of hematopoietic cells, the production of which has been increased by contact with a Therapeutic of the invention. In a particular embodiment, the pharmaceutical composition contains hematopoietic cells made recombinant by gene therapy methods. These hematopoietic cells can be provided to a patient by any method known in the art, preferably by intravenous delivery. Various delivery systems are known and can be used to administer a Therapeutic of the invention, e.g., encapsulation in liposomes, microparticles, microcapsules, recombinant cells capable of expressing the Therapeutic, receptor-mediated endocytosis (see, e.g., Wu and Wu, 1987, J. Biol. Chem. 262:4429–4432), construction of a Therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent. It may be desirable to administer the pharmaceutical compositions of the invention locally to the area in need of treatment; this may be achieved, for example and not by way of limitation, by topical application, by injection, by means of a catheter, by means of a suppository, or by means of an implant, said implant being of a porous, non-porous, or gelatinous material, including membranes, such as sialastic membranes, or fibers.

In one embodiment, the Therapeutic can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In another embodiment, the Therapeutic can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres, Boca Raton, Fla. (1974); Controlled Drug Bioavailability, Drug Product Design and Performance, Smolen and Ball (eds.), Wiley, N.Y. (1984); Ranger and Peppas, J. Macromol. Sci. Rev. Macromol. Chem. 23:61 (1983; see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the Therapeutic is a nucleic acid encoding a protein Therapeutic, the nucleic acid can be administered by gene therapy methods as described supra Section 5.1.4.

The present invention also provides pharmaceutical compositions. Such compositions comprise an amount of a Therapeutic effective to increase hematopoietic cell production, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the Therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention or titer of hematopoietic cells or recombinant hematopoietic cells which will be effective in the treatment of a particular disorder or condition will depend on the nature of the disorder or condition, and can be determined by standard clinical techniques. In addition, in vivo and/or in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. For example, therapy of at least 15,000 I.U. and up to 45,000 I.U. hCG weekly was shown to be effective and well tolerated in humans. Weekly doses of 6,000 I.U. in monkeys and 300–500 I.U. in mice were also shown to be effective. Additionally, predicted suitable doses of a β-hCG peptide for treatment or prevention of diseases and disorders in which increased numbers of one or more hematopoietic cell types are desirable include, but are not limited to, 1 to 1000 micrograms per week. Routes of administration of a Therapeutic include, but are not limited to, subcutaneously, intramuscularly or intravenously. Effective doses may be extrapolated from dose-response curves derived from in vitro or animal model test-systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

7. Example: Effects of Preparations of hCG, β-hCG and B-hCG Peptides on Hematopoiesis Human Chorionic Gonadotropin (hCG), a glycoprotein hormone produced in early pregnancy, consists of two sub-units, α and β, which associate non covalently to form a heterodimer which embodies its hormonal activity. Here we report that some partially purified preparations of hCG and β-hCG and some β-chain fragments stimulate the growth of hematopoietic progenitors. We have named these active β-hCG peptides "satellins". Satellin A, the most active peptide, represents the β-hCG fragment spanning amino acids 45–57 (SEQ ID NO:6) while satellin B, also with some activity, spans 109–119 of the β-chain. Furthermore, in 3 of 3 SIV acutely infected rhesus macaque monkeys the same preparation of hCG (pre-screened for anti viral activity) at a dose of 6,000 IU per week, led to a reduction of SIV in plasma, an increase in CD4$^+$ T cells and weight gain. Examples of pro-hematopoietic effects are observed in prelimirary studies of a limited number of patients treated with some commercial hCG products Factors such as patient stage, total weekly dose, and manufacturer source very likely play a role in the variability of response.

7.1. Effects of hCG Preparations in SIV Infected Rhesus Monkeys

Events early in HIV infection are thought to be critical to subsequent AIDS pathogenesis. However, early events in HIV infection in humans are difficult to study, but can be readily investigated in the SIV infected rhesus monkey animal model. (Letvin et al., 1990, *J. AIDS* 3:1023–1040). SIV and HIV-1 are similar in many of their biological and physical properties including their genomic structure. In addition, SIV$_{mac251}$, unlike several other SIV isolates, induces a syndrome in experimentally infected rhesus macaques that is similar to human AIDS (Kestler et al., 1990, *Science* 248:1109–1112).

The effect of the same commercially available hCG preparation (APL, Wyeth Ayerst), which had been pre-screened for anti-viral and anti-KS activity, was studied in five adult male rhesus monkeys who were intravenously inoculated with cell free SIV$_{mac251}$ ($10^{4.5}$ TCID$_{50}$/ml). In all animals, SIV p27 was apparent in plasma 14 days after infection, reaching a maximum by about day 20 (not shown). Treatment with systemic injections (3,000 IU, 2 times weekly) of the active commercial preparation of hCG (APL), was initiated 3 weeks after SIV inoculation. Two months post-inoculation, the characteristic increase of SIV p27 antigen (FIG. 1A), reduction of CD4$^+$ T cells (FIG. 1B), and weight loss (FIG. 1C) occurred in 2 of 2 untreated infected monkeys. In contrast, the 3 infected monkeys treated with this hCG preparation showed weight gain characteristic of uninfected animals of this age: 2–4 kg (FIG. 1C), a marked decrease in SIV p27 (FIG. 1A) and an increase in CD4$^+$ T cells to normal levels (FIG. 1B) which were maintained over the 7 months the animals were followed. These results show that this commercially available hCG preparation can control SIV$_{mac251}$ acute infection, increase CD4$^+$ T cells, and promote weight gain in SIV infected rhesus monkeys and that these effects can be maintained. The animals were followed for 7 months and no evidence of disease or SIV resistance to the hCG preparation developed.

Figure 1D:
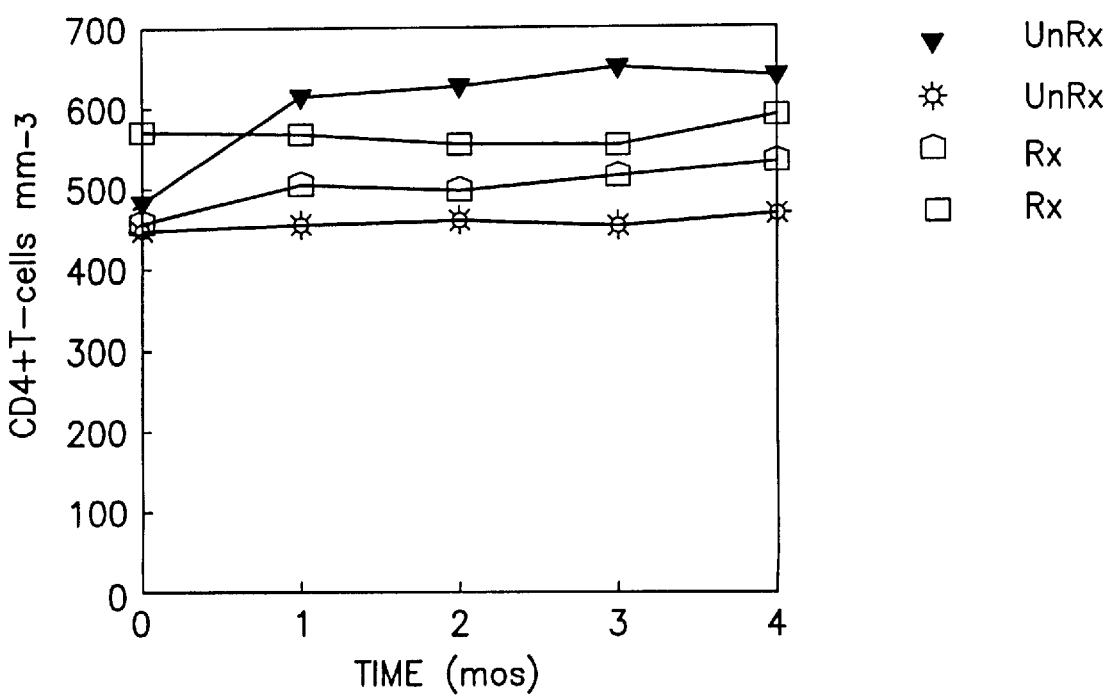

In FIG. 1D, results are shown from 4 uninfected controls. 2 received the hCG preparation and 2 received the diluent without the hCG. There is a slight increase in the CD4$^+$ T cells in the treated animals (increasing from 460 mm$^3$ to 520 mm$^3$ and from 470 mm$^3$ to 650 mm$^3$) (FIG. 1D). The 2 treated animals also showed a 1 to 2 kg weight gain (not shown.)

7.2. Early Studies of some hCG Preparations in Patients with HIV-1 Disease

The incidence of KS is greatly increased in HIV-infected persons (Friedman-Kien et al., 1981, *J. Am. Acad. Dermatol.* 5:468–473). Based on experimental studies of the killing effect of some hCG preparations on KS1 cells, clinical trials with some commercially available preparations of hCG given either intralesionally (Hermans et al., 1995, *Cellular and Molecular Biology* 3:357–364; Gill et al., 1996, *NEJM* (in press); Harris, P. J., 1995, *The Lancet* 346:118–119) or systemically to KS patients have shown that cutaneous KS lesions were reduced via cell killing by apoptosis following intralesional inoculation (Lunardi-Iskandar et al., 1995, *Nature* 375:64–68; Hermans et al., 1995, *Cellular and Molecular Biology* 3:357–364; Gill et al., 1996, *NEJM* (in press)) and induced regression of advanced KS disease treated by systemic delivery.

Early clinical and laboratory data from 46 patients (Table 2) treated on two protocols as well as some treated under IRB sanctioned compassionate use, provide instructive examples of the effects of two hCG preparations, APL (Wyeth Ayerst) and Pregnyl (Organon) in patients at various stages of HIV infection. Early clinical. experience with relatively low dose intralesional hCG administration for KS documented partial or complete regression of treated lesions including 3 of the first 4 patients in the initial pilot study in Belgium (Hermans et al., 1995, *Cellular and Molecular Biology* 3:357–364) (patients from Belgian study denoted as "PH" in Table 2) as well as a dose dependent effect between 16% (250 IU) and 83% (2,000 IU) in patients reported from California (Gill et al., 1996, *NEJM* (in press)) (patients from California study denoted as "PG" in Table 2), and other cases showing striking clearance of viscera (lung and gastrointestinal) KS in very advanced disease following systemic therapy with hCG APL or Pregnyl within 1 to 3 months of initiating therapy. In some instances there has been time for long-term evaluation in KS patients and AIDS patients without KS (see below).

AIDS patients treated with hCG therapy were tested for increases in CD4$^+$ T cell levels (in numbers of cells per mm$^3$) and decrease in viral load by one of the following assays for determining viral load: NASBA (Louache, et al., 1992, *Blood* 180:2991–2999; Geller, et al., 1985, *Archs. Path. Lab. Met.* 109:138–145), which has a lower detection limit of 4,000 copies; Roche Amplicor, with a lower detection limit of 200 copies; RT-PCR, with a lower detection limit of 100 copies; or TCID assay in which the infection of PBMCs in co-culture is determined (Popovic et al., 1984, *Science* 204:309–321). Patients were also examined for weight change (in kilograms) and for changes in Kaposi's sarcoma disease. Illustrative examples of the long-term effect of an hCG preparation in advanced AIDS are described below:

As shown in FIGS. 2A and B, the first patient, PH-VE, with cutaneous KS, who enrolled in the formal trial in Belgium and has now been followed for 80 weeks, .experienced an increase in CD4$^+$ T cell levels from 100 mm$^3$ to 160 mm$^3$ and a 1.5 log decrease in viral load from 230,000 copies to 11,000 copies by NASBA assay following relatively low dose intralesional injections and subsequent subcutaneous injections for 6 weeks (FIGS. 2A and B). The patient has continued therapy over 72 weeks, and viral load, as measured by RT-PCR, has been maintained at a low level (2,500 to 100 viral copies) and CD4$^+$ T cells have remained stable at 204 mm$^3$ at 68 weeks of hCG therapy (FIG. 2A). A recent KS relapse responded to higher dose hCG treatment (30,000 IU/week).

Figure 2C:
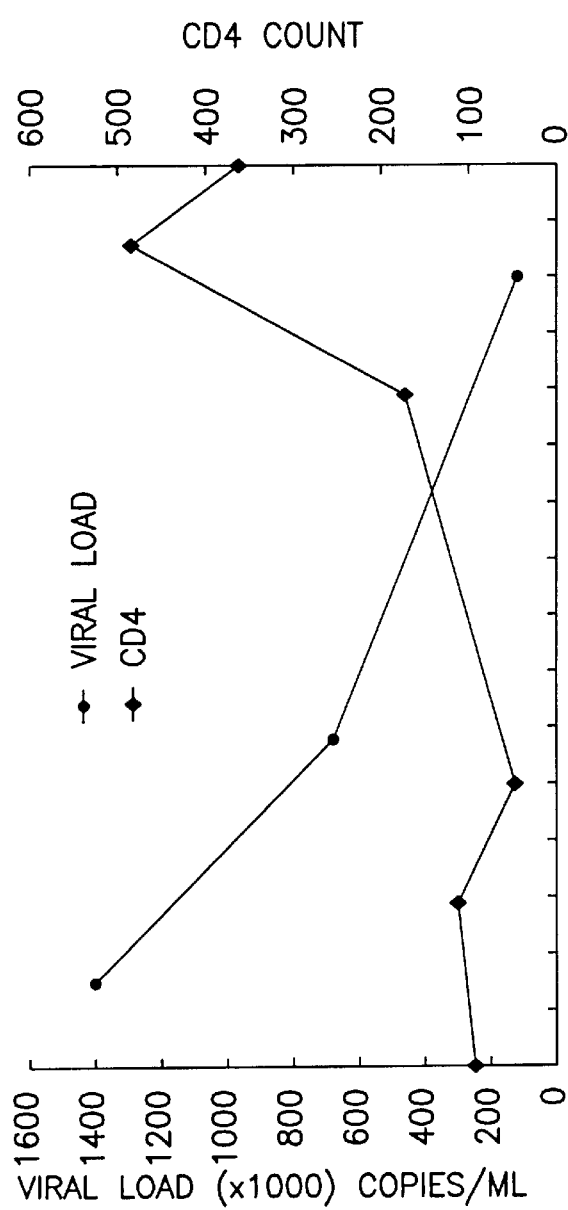
Figure 2D:
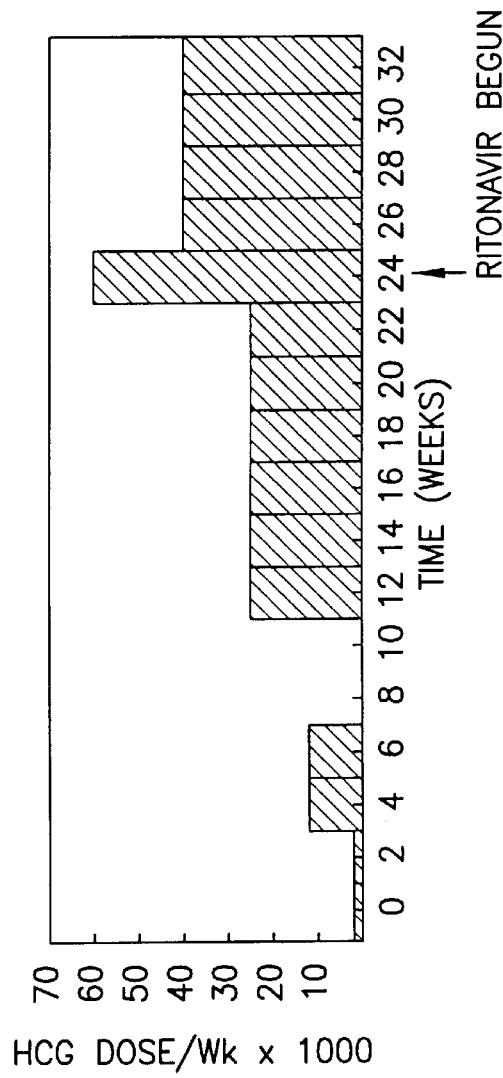

Patient PH-SPBE (FIGS. 2C and D) is illustrative of the synergistic effects of treatment with the hCG preparation followed by antiviral chemotherapy. Following an initial intralesional protocol for 6 weeks, the patient was taken off of hCG therapy for 4 weeks, and then was administered systemic doses of 25,000 IU, followed by 40,000–60,000 IU per week (FIG. 2D). As shown in FIG. 2C, viral load, as measured by NASBA assay, declined from 1,400,000 copies to 700,000 copies and CD4$^+$ T cells stabilized in the mid-100 mm$^3$s. At 22 weeks, Ritonavir therapy was added and subsequent viral load was reduced further and CD4$^+$ T cells rose to over 300 mm$^3$ (FIGS. 2C and D).

Patient PH-OJ (FIGS. 2E and F), who was severely immunosuppressed with CD4$^+$ T cells below 10 mm$^3$, experienced a viral load drop as measured by RT-PCR from 100,000 to 2500 copies after treatment with hCG, but did not experience an increase in CD4$^+$ T cell levels (FIG. 2E). Recently, while on higher doses of hCG (APL), hCG therapy was discontinued because of exacerbation of preexisting cholestasis which required hospitalization.

Of 15 protocol patients from the Belgium trial, an additional 4 had KS responses by ACTGO criteria including several with improved CD4$^+$ T cells and viral load patterns. The non-responders often had very advanced disease and several died during the period of follow-up (Table 2). While viral load and/or CD4$^+$ T cell data were available only for a subset of 29 patients (Table 2), some patients did exhibit increases in CD4$^+$ T cells and some patients also exhibited 1 log or more decreases in viral load (Table 2) without any change in their antiviral therapy.

An additional 10 patients from the Belgium study with advanced disease, some with visceral KS involvement, were treated systemically with higher doses of hCG (15,000 to 30,000 IU) (Table 2). Four have not responded, including 1 who died from opportunistic infection. The remaining 6, however, showed marked responses, including 4 who experienced 75% or more complete regression of visceral KS (Patients PO-DU, PO-GE, PH-JPV, PH-RF), and one (Patient PH-RF) who also demonstrated a decline of viral load from 69,000 copies to less than 4000 copies by NABSA assay (below lower detection limit for the assay).

A recently implemented trial (other "PG" patients in Table 2) employing systemic hCG therapy confirmed a substantial anti-KS effect in 4 of the 5 patients followed for more than 4 months and stabilization of lesions in some patients followed for shorter periods. In one patient (PG-4) on no other antiviral therapy, CD4$^+$ T cell levels rose 10 fold from 47 mm$^3$ to 424 mm$^3$. CD4$^+$ T cell levels in the other patients on anti-virals, including protease inhibitors, were stable or increased. Declines in viral load were noted in several patients, including a 1 log drop in PG-1 (who was on reverse transcriptase inhibitors at enrollment) while stable viral load or demonstrated increases in viral load were noted in other patients (e.g., PG-3 on multiple drugs and PG-15 on no other therapy).

Summarized in Table 2 are the data on 16 patients with paired pre- and post-treatment viral load measurements assayed by either NASBA, Roche Amplicor, or RT-PCR, and 13 patients with paired CD4+ T cell levels and no viral load measurements. In some patients following hCG therapy there were substantial declines in viral load and/or an increase of CD4+ T cells. Since the majority of patients when entered on therapy were also on single or multiple drug anti-viral inhibitors, synergistic effects cannot be ruled out, although some patients showed viral load declines and/or CD4+ T cell increases on hCG alone. Weight gain was recorded in a substantial portion of patients, even some who were in the most advanced stages of HIV infection. Increased appetite and improved sense of well being were also reported. Patient PH-DP with CDC stage B1-HIV disease without KS and with no change in preexisting anti-viral therapy experienced a 2 log reduction in viral load as measure in the TCID assay.

It is important to emphasize that there is potential for selection against obtaining positive "hCG" responses in these treated patients. For example, in some patients with advanced disease, only those who responded to "hCG" therapy at lower doses (less than 15,000 IU total weekly) (e.g., PR-VE, PH-MP) were given further "hCG" therapy, including high doses, while treatment was discontinued in those who did not respond at the lower dose (e.g., PH-LFA, PO-LC, PO-CJP, PO-BO, PO-RB Table 2). Thus, the potential for a higher dose effect was not evaluated in those patients who did not respond to the lower doses. For example, in patient PH-GA, stabilization of disease was seen at week 6, but complete regression was not recorded until week 14. Responses of patients to dosages of 30,000 to 45,000 IU, particularly the 4 of 5 patients who exhibited regression of KS disease with at least 4 months of follow-up in the initial data from the systemic protocol (35,000 IU/week) encourage the belief that higher doses of some hCG preparations will lead to more consistent beneficial responses. In view of the positive results in these patients, the lack of significant toxicity of these hCG preparations, coupled with the results in monkeys (FIGS. 1A–C) in which a far higher dose was used (considering body weight), it is evident that "non-responders" studied here merit therapy at higher dose level before concluding that any represent true failure to respond.

TABLE 2

Clinical details of patients treated with an hCG preparation

| Patient ID | Duration of Rx (weeks) | Diagnosis | Weekly Dose hCG/IU | CD4/mm³ PreRX | Rx | Viral Load PreRx | Rx | Weight gain Kg | KS response PR = Partial Regression CR = Complete Regression PF = Progressive Disease |
|---|---|---|---|---|---|---|---|---|---|
| PH-VE[a,b] | 80+ | KS-C | 12,500 P 30,000 P(M20) | 105 | 160(M4) 204(M20) | 230,000 N | 11,000 | +6 | PR |
| PH-OJ[b] | 31+ | KS-C | 12,506 P | 14 | 3(M4) | 100,000 R | 2,500R | +3 | PR |
| PH-GF | 18+ | KS-C | 12,500 P | 3 | 35(M2) | 1,100,000 N | 150,000 N | +2 | PR |
| PH-SPBE[b] | 29+ | KS-C | 25,000 PA | 48 | 174(M3) | 1,400,000 N | 770,000 | +1 | PR |
| PH-RF[b] | 12+ | KS-V | 15,000 P | 0 | 17(M3) | 69,000 N | <4000 N | +1 | PR |
| PH-DP[b] | 8+ | No KS | 30,000 P | 517 | NA | 100 T | 1T (1 mo) | ND | NA |
| PH-JPV | 8+ | KS-V | 15,000 P | <50 | NA | NA | NA | NA | CR |
| PH-LE | 12+* | KS-VC | 30,000 P | <5 | <5(M1) | NA | NA | NA | Stable |
| PH-MP | 24+* | KS-C | 30,000 P | 360 | 505(M3) | NA | NA | +3 | CR |
| PH-GRX[b] | 17+* | KS-C | 12,500 P | 97 | 89(M2) | NA | NA | −3(diet) | PR |
| PH-GA | 12+ | KS-C | 15,000 | 10 | NA | 2,500 R | 500 R | 0 | CR |
| PH-SP[b] | 8+* | KS-VC | 30,000 P | 6 | 5(M1) | NA | NA | 0 | PD |
| PO-FY[b] | 6+* | KS-C | 12,500 P | 180 | 202(M2) | NA | NA | +1.5 | PD |
| PO-GE[b] | 48+* | KS-VC | 15,000 P | 10 | 10(M4) | NA | NA | 0 | CR |
| PO-DU[b] | 37+ | KS-VC | 12,500 P | 5 | 10(M2) | 420,000 N | 300,000 | +2 | Stable |
| PO-LC[b] | 12+ | KS-VC | 12,500 P | 70 | 72(M3) | NA | NA | +1.5 | PD |
| PO-CJP[b] | 6+ | KS-C | 12,500 P | 14 | 14(M1.5) | NA | NA | +1 | PD |
| PO-BO[b] | 6+ | KS-C | 12,500 P | 12 | 12(M1.5) | NA | NA | +1.5 | PD (Died) |
| PO-RB[b] | 4+ | KS-VC | 12,500 P | 50 | 35(1M) | NA | NA | +1 | PD (Died) |
| PG-1[b] | 16+ | KS-C | 35,000 A | 63 | 170(M4) | 75,000 A | 1,700 A | −0.9 | PD |
| PG-3[b,c] | 16+ | KS-C | 35,000 A | 37 | 48(M4) | 52,000 A | 40,000 A | +1.8 | CR |
| PG-4 | 16+ | KS-C | 35,000 A | 47 | 424(M4) | 80,900 A | 55,000 A | +1.4 | Stable |
| PG-6[b,c] | 12+ | KS-C | 35,000 A | 29 | 21(M3) | 62,500 A | 98,000 A | +3.2 | Stable |
| PG-7 | 10+ | KS-C | 30,000 A | 108 | 213 | NA | NA | +4.5 | PR |
| PG-8 | 12 | KS-C | 30,000 A | 787 | 678 | 60,760 A | 22,313 A | +2.3 | PD |
| PG-9 | 11+ | KS-C | 30,000 A | 123 | 218 | NA | NA | −5.0 | Stable |
| PG-10[b] | 12 | KS-C | 30,000 A | 82 | 86 | 25,364 A | 6,777 A | +2.3 | Stable |
| PG-11[b] | 4.5 | KS-C | 30,000 A | 218 | 361 | 661 A | 200 A | +5.4 | Stable |
| PG-12 | 19+ | KS-C | 30,000 A | 22 | 46 | NA | NA | +10.0 | PR |
| PG-15 | 8 | KS-C | 70,000 A | 388 | 483 | 6,162 A | 22,510 A | +1.8 | PD |

*Only patients with CD4+ T-cell and/or viral load data are included. Patients who began protease inhibitors at the beginning or during hCG therapy or who did not comply with hCG therapy (PG-17) are excluded. preRx = before treatment with hCG; Rx = post treatment with hCG.
[a]Data on PH-VE are presented in the text reporting stabilization of CD4 levels over 20 months of hCG monotherapy and persistently low viral load by RT-PCR (range 500 to 12,500) with escalating doses of hCG from 15,000 IU (52 weeks) to 30,000 IU per week (Pregnyl) recently which resulted in regression of recurrent cutaneous KS.
[b]Patient was on nucleoside/non-nucleoside reverse transcriptase inhibitors when hCG treatment began.
[c]Patient was on protease inhibitors when hCG started. The following indicate response of Kaposi's Sarcoma to treatment: PD indicates progressive disease; CR indicates complete response; and PR = Partial response.
NA represents data not available. The hCG commercial preparations administered are indicated by P for Pregnyl and A for APL.
M represents month from enrollment on protocol. Viral load techniques used are indicated by R for RT-PCR; N for NASBA; T for TCID; A for Roche Amplicor.
Under the diagnosis column, KS represents Kaposi sarcoma; KS-V represents KS with visceral involvement; KS-C represents KS with cutaneotis lesions only; KS-VC represents KS with both visceral and cutaneous involvement.

Patient Information

A total of 46 patients were available for analysis of whom 30 are included in Table 2 because serial viral load data and/or CD4+ T cell counts were recorded. Twenty-eight patients were treated in Belgium, either on a protocol to investigate intralesional and systemic treatment of cutaneous KS (n=15), or in the pre-clinical phase of that protocol (n=3), or on compassionate use for systemic KS or HIV infection (n=10). The protocol involved intralesional administration of 500 IU hCG (Pregnyl) to 4 lesions for 2 weeks, followed by subcutaneous administration of 2,500 IU hCG (Pregnyl) 5 days per week for 4 to 6 weeks. Additional systemic intramuscular or subcutaneous hCG treatment with either Pregnyl, APL, or Steris (one patient) was provided as ongoing therapy in some patients or as part of compassionate use protocols.

A total of 18 patients were treated in California with at least 1 month of follow-up as part of an ongoing protocol to evaluate systemic hCG therapy for cutaneous KS. These patients received either 5000 IU of APL subcutaneously 7 days per week, 10,000 IU subcutaneously 3 times per week, or 10,000 IU subcutaneously 7 days per week. Five of the systemic cases are not shown because of absent baseline viral load measurements. Five patients with serial viral load measurements started protease inhibitors during the course of hCG therapy and their viral load data is not listed: PG2, who had viral load measurement of 10,496 copies before starting the hCG therapy and a last measurement of 15,542 copies (Roche Amplicor test), started Norvir after hCG; PG5, for whom there was no viral load data started Norvir after hCG; PG-16, had a viral load measurement of 47,931 copies before starting hCG therapy and a last measurement of 370 copies, started Ritonavir after hCG; PG-18, with a viral load of 3673 copies before hCG therapy and a last viral load measurement of 1742 copies, started Crixivan after hCG; PH-SPBE had a viral load of 120,000 copies (NASBA test) compared to the value of 770,000 copies before Ritonavir was added to ongoing hCG treatment; and PH-JPV, had a viral load of 500,000 copies (Roche Amplicor test) before starting hCG therapy and by week 4 of hCG alone, had a viral load of 4,900,000 copies and exhibited undetectable viral load following indinavir (Crixivan) which was added after hCG induced pulmonary response.

Overall 28 patients were on pre-existing, anti-viral therapy (RT inhibitors), 11 were on no anti-virals and 7 were missing information. One patient, PH-RF, was on 3TO therapy before hCG therapy, and despite poor compliance, had an hCG response for visceral KS and viral load, which declined to undetectable on hCG alone.

Thirty-six patients survived the study, 7 (PH-LFA, PH-DD, PH-PJ, PO-BO, PO-RB, PH-JJ, PH-MH) died either from opportunistic infections or multiple organ failure. The vital status of 1 patient is unknown. Two patients, PH-DD and PH-OJ discontinued hCG treatment because of cholestasis. PH-DD was on concomitant anti-mycobacterial therapy which was felt to be a contributing factor. PH-OJ had preexisting cholestasis. When hCG was restarted recently, cholestasis was exacerbated with a marked increase in alkaline phosphatase and rise in bilirubin which required hospitalization. These values declined by 2-fold following discontinuation of hCG. These cases raise the possibility that liver toxicity may be a rare complication of hCG therapy. Among the patients not listed in Table 2, 2 (PG2 and PG5) are on systemic hCG and have exhibited a KS response; 7 (PH-JJ, PH-MH, PH-LG, PH-JPV, PG-16, PG-18) had partial responses; 2 (PO-SC, and PH-LFA) did not respond to hCG or their disease progressed on therapy; 2 (PG-13 and PG-14) are currently in follow-up, but not evaluable; and 4 (PH-PJ, PH-DP, PH-GL, PG17) could not be evaluated or were lost to follow-up. PO-DU experienced stabilization of pulmonary disease and recently developed 2 new cutaneous lesions which responded to radiation therapy without any change in his pulmonary KS. PO-GE experienced complete response to cutaneous and pulmonary KS on hCG alone, PH-RF with gastric KS experienced a marked decline in viral load and a 75% decline and subsequent stabilization of pulmonary KS on hCG, and PH-JPV with pulmonary and gastric KS dramatically improved his pulmonary function test after one month of hCG alone.

7.3. Effects of hCG and 8-hCG Peptides on Hematopoiesis

In addition to the typical decline in CD4+ T cells, cytopenias can occur in HIV infected people affecting one or more hematopoietic lineages associated with deficient progenitor cell growth. This is often made worse by some of the anti-viral therapies currently in use. In contrast, hCG preparations do not inhibit hematopoiesis.

The effect of hCG preparations and peptides was assayed on hematopoietic progenitor cells in vitro. Hematopoietic progenitor cells ($2\times10^5$ cell/ml) were isolated from normal bone marrow and cord blood and seeded in methylcellulose. The amount of various hCG preparations and peptides used in these clonogenic assays were: hCG. (APL): 200 IU/ml; hCG alpha subunit (Sigma): 100 µg/ml; purified hCG heterodimer CR 127: 200 IU/ml; β-hCG peptide 109–119 (SEQ ID NO:7) (Bachem): 100 µg/ml (83 nmoles); β-hCG peptide 45–57 (SEQ ID NO:6): 100 µg/ml (67 nmoles); β-hCG peptide 45–57c circularized (44–57 with cysteine substituted for the amino acid at position 44 (SEQ ID NO:26)): 100 µg/ml; mixture of scrambled β-hCG peptides 45–57 and 109–119: 100 µg/ml; and crude preparation of native β-hCG: 100 µg/ml. The native commercial preparation of hCG (APL, Wyeth Ayerst) was pre-tested (for anti-HIV and anti-KS activities). Aggregates containing more than 50 cells after 10 days of culture were counted as colonies.

As shown in FIGS. 3A–C, the growth of hematopoietic progenitors (Lunardi-Iskandar et al., 1989, *Leukemia Res.* 13:573–581) is directly promoted by a commercial preparation of partially purified hCG (APL, Wyeth Ayerst), partially purified native β-chain, and by the synthetic peptides, β-hCG peptide 45–57 (SEQ ID NO:6) and β-hCG peptide 109–119 (SEQ ID NO:7), respectively) and circularized 44–57 with cysteine substituted for the amino acid at position 44 (SEQ ID NO:26), but not by the pure hCG heterodimer (CR127) nor by the pure (recombinant) β-chain or the α-chain. The following peptides were tested and showed little or no effects in hematopoiesis assays: α-hCG peptide of amino acids 88–92, and the β-hCG peptides of amino acids 6–16, 7–40, 34–49, 38–57, 57–93, 74–95, 100–110, 123–145, 134–144. Additionally, scrambled β-hCG peptides 45–57 and 109–119 showed little inhibition. Thus, these results recapitulate the anti-KS and anti-HIV effects. Each activity is chiefly effected by the satellin peptides. A series of other peptides of the α- and β-chain had no effect (data not shown).

7.4. Discussion

We found considerable pro-hematopoietic activity with the native partially purified hCG heterodimer and whole β-chain, however, variability in the pro-hematopoietic effect was observed for different hCG preparations and no pro-hematopoietic activity was observed with highly purified (to homogeneity) hCG heterodimer in vitro. We suspect that the lower molecular weight species may retain the pro-hematopoietic effect and that some purification procedure may not eliminate those species.

The available clinically used native hCG and native β-chain preparations are not homogenous and may be contaminated with one or more other active molecules. In this respect, it is noteworthy that though the effects of some preparations of hCG described here were obtained with two different commercial sources of hCG (APL and Pregnyl), one was usually more active (APL) at lower concentrations than any other preparation. The differences in activities of commercial preparations might be explained by variation in the amount of β-hCG fragments. This could be the consequence of different methods of preparation or different sources of human urine. For example, free β is more abundant in the earliest weeks of pregnancy. Consequently, we initiated studies with a variety of synthetic peptides, and our results show that all the in vitro activities of the preparations of native hCG are mimicked by the β-hCG peptides 45–57 and 109–119 but not other β- or α-peptides or scrambled 45–57 peptide. Thus, we suggest that β-hCG contains structural motifs that produce effects which probably work by mechanisms which differ from those currently known for hCG. We suspect that β-hCG peptides have biological functions quite distinct from the conventional effects of the heterodimer. In view of the evidence that the a subunits are needed for binding to the hCG receptor, we are uncertain now the β peptides initiate these effects. Thus, whether the effects we have observed are mediated by known hCG receptors is unknown. Given that the mechanism of action of these hCG peptides is likely to involve pathways distinctive from normal hCG hormonal pathways, it is proposed that these active peptides represent a new class of active molecules which we named Satellins. The first members of this class are Satellin A for the active moiety from the β-hCG peptide 45–57 and Satellin B for the 109–119 fragment.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references are cited herein, the disclosures of which are incorporated by reference in their entireties.

What is claimed is:

1. A method for increasing production of one or more hematopoietic cell types in a subject in need thereof, said method comprising administering to the subject in need thereof an amount of a circularized peptide which amount is effective to increase the production and/or maintain increased production of one or more hematopoietic cell types in the subject, said peptide comprising an amino acid sequence consisting of a fragment of β-hCG (SEQ ID NO:2) selected from the group consisting of: 41–54, 45–54, 47–53, 45–57, 45–58, 41–53, 42–53, 43–53, 44–53, 44–57, 45–53, 46–53, 45–55, 45–56, 47–54, 47–55, 47–56, 47–58, 48–145, 58–145, 109–119, and 109–145 (SEQ ID NOS: 3–6, 18, 8–14, 16, 17, 19–24, 7 and 25 respectively), said peptide excluding β-hCG amino acids contiguous to said fragment, and said peptide excluding an amino acid sequence consisting of the entire β-hCG chain, said sequence having at least two cysteine residues, optionally wherein:

(a) at least one of the cysteine residues has been inserted between two non-cysteine amino acid residues;

(b) at least one of the cysteine residues has been coupled at an end of the amino acid sequence; and/or (c) at least one non-cysteine amino acid residue has been replaced by a cysteine residue;

wherein two cysteine residues are coupled together by a disulfide bond, said circularized peptide being active to increase the production of one or more hematopoietic cell types.

2. The method of claim 1 wherein the fragment of β-hCG is 41–54 (SEQ ID NO: 3).

3. The method of claim 1 wherein the fragment of β-hCG is 45–54 (SEQ ID NO: 4).

4. The method of claim 1 wherein the fragment of β-hCG is 47–53 (SEQ ID NO: 5).

5. The method of claim 1 wherein the fragment of β-hCG is 45–57 (SEQ ID NO: 6).

6. The method of claim 1 wherein the fragment of β-hCG is 45–58 (SEQ ID NO: 18).

7. The method of claim 1 wherein the fragment of β-hCG is 41–53 (SEQ ID NO: 8).

8. The method of claim 1 wherein the fragment of β-hCG is 42–53 (SEQ ID NO: 9).

9. The method of claim 1 wherein the fragment of β-hCG is 43–53 (SEQ ID NO: 10).

10. The method of claim 1 wherein the fragment of β-hCG is 44–53 (SEQ ID NO: 11).

11. The method of claim 1 wherein the fragment of β-hCG is 44–57 (SEQ ID NO: 12).

12. The method of claim 1 wherein the fragment of β-hCG is 45–53 (SEQ ID NO: 13).

13. The method of claim 1 wherein the fragment of β-hCG is 46–53 (SEQ ID NO: 14).

14. The method of claim 1 wherein the fragment of β-hCG is 45–55 (SEQ ID NO: 16).

15. The method of claim 1 wherein the fragment of β-hCG is 45–56 (SEQ ID NO: 17).

16. The method of claim 1 wherein the fragment of β-hCG is 47–54 (SEQ ID NO: 19).

17. The method of claim 1 wherein the fragment of β-hCG is 47–55 (SEQ ID NO: 20).

18. The method of claim 1 wherein the fragment of β-hCG is 47–56 (SEQ ID NO: 21).

19. The method of claim 1 wherein the fragment of β-hCG is 47–58 (SEQ ID NO: 22).

20. The method of claim 1 wherein the fragment of β-hCG is 48–145 (SEQ ID NO: 23).

21. The method of claim 1 wherein the fragment of β-hCG is 58–145 (SEQ ID NO: 24).

22. The method of claim 1 wherein the fragment of β-hCG is 109–119 (SEQ ID NO: 7).

23. The method of claim 1 wherein the fragment of β-hCG is 109–145 (SEQ ID NO: 25).

24. The method of claim 1 wherein the subject is a primate.

25. The method of claim 1 wherein the subject is a human.

26. The method of claim 1 wherein the peptide is administered at least once per week.

27. The method of claim 1 wherein the peptide is administered at least twice per week.

28. The method of claim 1 wherein the peptide has the following formula:

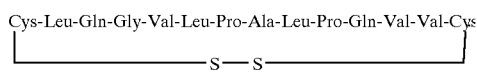

29. A method for increasing production of one or more hematopoietic cell types in a subject in need thereof, said method comprising administering to the subject in need thereof an amount of a pharmaceutical composition comprising:

(a) a circularized peptide comprising an amino acid sequence consisting of a fragment of β-hCG (SEQ ID NO:2) selected from the group consisting of: 41–54, 45–54, 47–53, 45–57, 45–58, 41–53, 42–53, 43–53, 44–53, 44–57, 45–53, 45–53, 45–55, 45–56, 47–54, 47–55, 47–56, 47–58, 48–145, 58–145, 109–119, and 109–145 (SEQ ID NOS: 3–6, 18, 8–14, 16, 17, 19–24, 7 and 25 respectively), said peptide excluding β-hCG amino acids contiguous to said fragment, and said peptide excluding an amino acid sequence consisting of the entire β-hCG chain, said sequence having at least two cysteine residues, optionally wherein:

(i) at least one of the cysteine residues has been inserted between two non-cysteine amino acid residues;

(ii) at least one of the cysteine residues has been coupled at an end of the amino acid sequence; and/or (iii) at least one non-cysteine amino acid residue has been replaced by a cysteine residue;

wherein two cysteine residues are coupled together by a disulfide bond, said circularized peptide being active to increase the production of one or more hematopoietic cell types; and (b) a pharmaceutically acceptable carrier.

30. The method of claim 29 wherein the fragment of β-hCG is 41–54 (SEQ ID NO: 3).

31. The method of claim 29 wherein the fragment of β-hCG is 45–54 (SEQ ID NO: 4).

32. The method of claim 29 wherein the fragment of β-hCG is 47–53 (SEQ ID NO: 5).

33. The method of claim 29 wherein the fragment of β-hCG is 45–57 (SEQ ID NO:6).

34. The method of claim 29 wherein the fragment of β-hCG is 45–58 (SEQ ID NO: 18).

35. The method of claim 29 wherein the fragment of β-hCG is 41–53 (SEQ ID NO: 8).

36. The method of claim 29 wherein the fragment of β-hCG is 42–53 (SEQ ID NO: 9).

37. The method of claim 29 wherein the fragment of β-hCG is 43–53 (SEQ ID NO: 10).

38. The method of claim 29 wherein the fragment of β-hCG is 44–53 (SEQ ID NO: 11).

39. The method of claim 29 wherein the fragment of β-hCG is 44–57 (SEQ ID NO: 12).

40. The method of claim 29 wherein the fragment of β-hCG is 45–53 (SEQ ID NO: 13).

41. The method of claim 29 wherein the fragment of β-hCG is 46–53 (SEQ ID NO: 14).

42. The method of claim 29 wherein the fragment of β-hCG is 45–55 (SEQ ID NO: 16).

43. The method of claim 29 wherein the fragment of β-hCG is 45–56 (SEQ ID NO: 17).

44. The method of claim 29 wherein the fragment of β-hCG is 47–54 (SEQ ID NO: 19).

45. The method of claim 29 wherein the fragment of β-hCG is 47–55 (SEQ ID NO: 20).

46. The method of claim 29 wherein the fragment of β-hCG is 47–56 (SEQ ID NO: 21).

47. The method of claim 29 wherein the fragment of β-hCG is 47–58 (SEQ ID NO: 22).

48. The method of claim 29 wherein the fragment of β-hCG is 48–145(SEQ ID NO: 23).

49. The method of claim 29 wherein the fragment of β-hCG is 58–145 (SEQ ID NO: 24).

50. The method of claim 29 wherein the fragment of β-hCG is 109–119 (SEQ ID NO: 7).

51. The method of claim 29 wherein the fragment of β-hCG is 109–145 (SEQ ID NO: 25).

52. The method of claim 29 wherein the subject is a primate.

53. The method of claim 29 wherein the subject is a human.

54. The method of claim 29 wherein the composition is administered at least once per week.

55. The method of claim 29 wherein the composition is administered at least twice per week.

56. The method of claim 29 wherein the composition has the following formula:

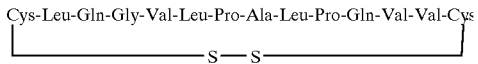

57. A circularized peptide for increasing the production of one or more hematopoietic cell types in a subject, said peptide consisting of a β-hCG fragment selected from the group consisting of β-hCG fragments 41–54, 45–54, 47–53, 45–57, 45–58, 41–53, 42–53, 43–53, 44–53, 44–57, 45–53, 46–53, 45–55, 45–56, 47–54, 47–55, 47–56, 47–58, 48–145, and 58–145, 109–119 and 109–145 (SEQ ID NOS: 3–6, 18, 8–14, 16, 17, 19–24, 7 and 25 respectively), wherein said peptide has at least two cysteine residues, optionally wherein:

(a) at least one of the cysteine residues has been inserted between two non-cysteine amino acid residues;

(b) at least one of the cysteine residues has been coupled at an end of the amino acid sequence; and/or (c) at least one non-cysteine amino acid residue has been replaced by a cysteine residue;

wherein two cysteine residues are coupled together by a disulfide bond, said circularized peptide being active to increase the production of one or more hematopoietic cell types.

58. The peptide of claim 57 wherein the fragment of β-hCG is 41–54 (SEQ ID NO: 3).

59. The peptide of claim 57 wherein the fragment of β-hCG is 45–54 (SEQ ID NO: 4).

60. The peptide of claim 57 wherein the fragment of β-hCG is 47–53 (SEQ ID NO: 5).

61. The peptide of claim 57 wherein the fragment of β-hCG is 45–57 (SEQ ID NO: 6).

62. The peptide of claim 57 wherein the fragment of β-hCG is 45–58 (SEQ ID NO: 18).

63. The peptide of claim 57 wherein the fragment of β-hCG is 41–53 (SEQ ID NO: 8).

64. The peptide of claim 57 wherein the fragment of β-hCG is 42–53 (SEQ ID NO: 9).

65. The peptide of claim 57 wherein the fragment of β-hCG is 43–53 (SEQ ID NO: 10).

66. The peptide of claim 57 wherein the fragment of β-hCG is 44–53 (SEQ ID NO: 11).

67. The peptide of claim 57 wherein the fragment of β-hCG is 44–57 (SEQ ID NO: 12).

68. The peptide of claim 57 wherein the fragment of β-hCG is 45–53 (SEQ ID NO: 13).

69. The peptide of claim 57 wherein the fragment of β-hCG is 46–53 (SEQ ID NO: 14).

70. The peptide of claim 57 wherein the fragment of β-hCG is 45–55 (SEQ ID NO: 16).

71. The peptide of claim 57 wherein the fragment of β-hCG is 45–56 (SEQ ID NO: 17).

72. The peptide of claim 57 wherein the fragment of β-hCG is 47–54 (SEQ ID NO: 19).

73. The peptide of claim 57 wherein the fragment of β-hCG is 47–55 (SEQ ID NO: 20).

74. The peptide of claim 57 wherein the fragment of β-hCG is 47–56 (SEQ ID NO: 21).

75. The peptide of claim 57 wherein the fragment of β-hCG is 47–58 (SEQ ID NO: 22).

76. The peptide of claim 57 wherein the fragment of β-hCG is 48–145 (SEQ ID NO: 23).

77. The peptide of claim 57 wherein the fragment of β-hCG is 58–145 (SEQ ID NO: 24).

78. The peptide of claim 57 wherein the fragment of β-hCG is 109–119 (SEQ ID NO: 7).

79. The peptide of claim 57 wherein the fragment of β-hCG is 109–145 (SEQ ID NO: 25).

80. The peptide of claim 57 having the following formula:

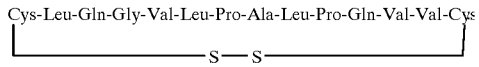

81. A pharmaceutical formulation comprising:

(a) A circularized peptide for increasing the production of one or more hematopoietic cell types in a subject, said peptide consisting of a β-hCG fragment selected from the group consisting of β-hCG fragments 41–54, 45–54, 47–53, 45–57, 45–58, 41–53, 42–53, 43–53, 44–53, 44–57, 45–53, 46–53, 45–55, 45–56, 47–54, 47–55, 47–56, 47–58, 48–145, 58–145, 109–119, and 109–145 (SEQ ID NOS: 3–6, 18, 8–14, 16, 17, 19–24, 7 and 25 respectively), wherein said peptide has at least two cysteine residues, optionally wherein:

(i) at least one cysteine residue has been inserted between two non-cysteine amino acid residues;

(ii) at least one cysteine residue has been coupled at an end of the amino acid sequence; and/or (iii) at least one non-cysteine amino acid residue has been replaced by a cysteine residue;

wherein two cysteine residues are coupled together by a disulfide bond, said circularized peptide being active to increase the production of one or more hematopoietic cell types; and (b) a pharmaceutically acceptable carrier.

82. The formulation of claim 81 wherein the fragment of β-hCG is 41–54 (SEQ ID NO: 3).

83. The formulation of claim 81 wherein the fragment of β-hCG is 45–54 (SEQ ID NO: 4).

84. The formulation of claim 81 wherein the fragment of β-hCG is 47–53 (SEQ ID NO: 5).

85. The formulation of claim 81 wherein the fragment of β-hCG is 45–57 (SEQ ID NO: 6).

86. The formulation of claim 81 wherein the fragment of β-hCG is 45–58 (SEQ ID NO: 18).

87. The formulation of claim 81 wherein the fragment of β-hCG is 41–53 (SEQ ID NO: 8).

88. The formulation of claim 81 wherein the fragment of β-hCG is 42–53 (SEQ ID NO: 9).

89. The formulation of claim 81 wherein the fragment of β-hCG is 43–53 (SEQ ID NO: 10).

90. The formulation of claim 81 wherein the fragment of β-hCG is 44–53 (SEQ ID NO: 10).

91. The formulation of claim 81 wherein the fragment of β-hCG is 44–57 (SEQ ID NO: 12).

92. The formulation of claim 81 wherein the fragment of β-hCG is 45–53 (SEQ ID NO: 13).

93. The formulation of claim 81 wherein the fragment of β-hCG is 46–53 (SEQ ID NO: 14).

94. The formulation of claim 81 wherein the fragment of β-hCG is 45–55 (SEQ ID NO: 16).

95. The formulation of claim 81 wherein the fragment of β-hCG is 45–56 (SEQ ID NO: 17).

96. The formulation of claim 81 wherein the fragment of β-hCG is 47–54 (SEQ ID NO: 19).

97. The formulation of claim 81 wherein the fragment of β-hCG is 47–55 (SEQ ID NO: 20).

98. The formulation of claim 81 wherein the fragment of β-hCG is 47–56 (SEQ ID NO: 21).

99. The formulation of claim 81 wherein the fragment of β-hCG is 47–58 (SEQ ID NO: 22).

100. The formulation of claim 81 wherein the fragment of β-hCG is 48–145 (SEQ ID NO: 23).

101. The formulation of claim 81 wherein the fragment of β-hCG is 58–145 (SEQ ID NO: 24).

102. The formulation of claim 81 wherein the fragment of β-hCG is 109–119 (SEQ ID NO: 7).

103. The formulation of claim 81 wherein the fragment of β-hCG is 109–145 (SEQ ID NO: 25).

104. The formulation of claim 81 wherein the circularized peptide has the following formula:

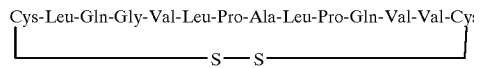

UNITED STATES PATENT AND TRADEMARK OFFICE
CERTIFICATE OF CORRECTION

PATENT NO. : 5,968,513

DATED : October 19, 1999

INVENTOR(S) : Robert C. Gallo; Joseph Bryant; Yanto Lunardi-Iskandar

It is certified that error appears in the above-indentified patent and that said Letters Patent is hereby corrected as shown below:

| | |
|---|---|
| Title Page, at [54]: | change "Method" to --Methods--. |
| Column 1, line 1: | change "Method" to --Methods--. |
| Column 2, line 2: | after "(503))" insert --,--. |
| Column 4, line 3: | change "cysteire" to --cysteine--. |
| Column 6, line 20: | after "recurred" insert --;--. |
| Column 13, line 48: | after "tuberculosis" insert --,--. |
| Column 14, line 54: | change "state etc. and" to --state, etc., and--. |
| Column 16, line 62: | change "CD34+" to --CD34$^{+}$--. |
| Column 17, line 1: | change "et al,.," to --et al.,--. |
| Column 17, line 4: | after "et al.," delete ".". |
| Column 18, line 12: | after "pool" insert --,--. |
| Column 19, line 62: | after "derivatives" insert --,--. |
| Column 20, line 42: | before "See" insert --(--. |
| Column 21, line 13: | after "deprotection" delete "to". |
| Column 21, line 43: | change "it" to --in--. |
| Column 23, line 2: | after "β-hCG" delete "a" and insert --amino acids--. |
| Column 24, line 32: | after "3" insert --'--. |
| Column 24, line 63: | change "733" to --703--. |
| Column 25, line 42: | change "Hemotopoirtic" to --Hemotopoietic--. |
| Column 26, line 34: | change "SIV$_{mac25}$," to --SIV$_{mac251}$--. |
| Column 28, line 5: | change "Liposomes in the " to --*Liposomes in the*--. |
| Column 28, line 20: | after "(1983" insert --)--. |
| Column 29, line 59: | after "test" delete "-". |
| Column 30, line 23: | change "prelimirary" to --preliminary--. |
| Column 30, line 24: | after "products" insert --.--. |
| Column 30, line 35: | after "model" delete ".". |
| Column 30, line 65: | after "months" insert --,--. |
| Column 31, line 1: | change "controls." to --controls:--. |

UNITED STATES PATENT AND TRADEMARK OFFICE
CERTIFICATE OF CORRECTION

PATENT NO. : 5,968,513
DATED : October 19, 1999
INVENTOR(S) : Robert C. Gallo; Joseph Bryant; Yanto Lunardi-Iskandar It is certified that error appears in the above-indentified patent and that said Letters Patent is hereby corrected as shown below:

Column 31, line 31: after "clinical" delete ".".
Column 31, line 41: change "viscera" to --visceral--.
Column 33, line 21: change PR-VE" to --PH-VE--.
Column 33, Table 2, 3rd Weekly Dose down: change "12,506P" to --12,500P--.
Column 35, line 35: change "3TO" to --3TC--.
Column 36, line 14: change "8-hCG" to --β-hCG--.
Column 36, line 27: after "hCG" delete ".".
Column 37, Sequence No:1 at 76 top: change "CTG" to --GTG--.
Column 38, line 5: change "now" to --how--.
Column 39, Sequence No:1 at 76 bottom: change "Leu" to --Val--.
Column 39, Sequence No:2 at 76: change "Leu" to --Val--.
Column 47, Sequence No:23 at 29: change "Leu" to --Val--.
Column 49, Sequence No:24 at 19: change "Leu" to --Val--.
Column 50, line 55: after "said" delete "peptide" and insert --amino acids--.
Column 52, line 10: delete "peptide" and insert --amino acids--.
Column 54, line 59: change "10" to --11--.
Column 56, line 9: at end of sentence after "Cy" insert --s--.
Column 52, line 5: change the second "45-53" to --46-53--.

Signed and Sealed this

Sixth Day of March, 2001

Attest:

NICHOLAS P. GODICI

Attesting Officer    Acting Director of the United States Patent and Trademark Office

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 539 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: CDS
      (B) LOCATION: 26..520

(xi) SEQUENCE DESCRIPTION: SEQ ID NO:1:

```
AGACAAGGCA GGGGACGCAC CAAGG ATG GAG ATG TTC CAG GGG CTG CTG CTG        52
                            Met Glu Met Phe Gln Gly Leu Leu Leu
                            -20                     -15

TTG CTG CTG CTG AGC ATG GGG GGG ACA TGG GCA TCC AAG GAG CCG CTT       100
Leu Leu Leu Leu Ser Met Gly Gly Thr Trp Ala Ser Lys Glu Pro Leu
    -10                 -5                   1

CGG CCA CGG TGC CGC CCC ATC AAT GCC ACC CTG GCT GTG GAG AAG GAG       148
Arg Pro Arg Cys Arg Pro Ile Asn Ala Thr Leu Ala Val Glu Lys Glu
                10                  15                  20

GGC TGC CCC GTG TGC ATC ACC GTC AAC ACC ACC ATC TGT GCC GGC TAC       196
Gly Cys Pro Val Cys Ile Thr Val Asn Thr Thr Ile Cys Ala Gly Tyr
            25                  30                  35

TGC CCC ACC ATG ACC CGC GTG CTG CAG GGG GTC CTG CCG GCC CTG CCT       244
Cys Pro Thr Met Thr Arg Val Leu Gln Gly Val Leu Pro Ala Leu Pro
        40                  45                  50

CAG GTG GTG TGC AAC TAC CGC GAT GTG CGC TTC GAG TCC ATC CGG CTC       292
Gln Val Val Cys Asn Tyr Arg Asp Val Arg Phe Glu Ser Ile Arg Leu
    55                  60                  65

CCT GGC TGC CCG CGC GGC CTG AAC CCC GTG GTC TCC TAC GCC GTG GCT       340
```

```
Pro Gly Cys Pro Arg Gly Leu Asn Pro Val Val Ser Tyr Ala Val Ala
 70                  75                  80                  85

CTC AGC TGT CAA TGT GCA CTC TGC CGC CGC AGC ACC ACT GAC TGC GGG        388
Leu Ser Cys Gln Cys Ala Leu Cys Arg Arg Ser Thr Thr Asp Cys Gly
             90                  95                 100

GGT CCC AAG GAC CAC CCC TTG ACC TGT GAT GAC CCC CGC TTC CAG GAC        436
Gly Pro Lys Asp His Pro Leu Thr Cys Asp Asp Pro Arg Phe Gln Asp
            105                 110                 115

TCC TCT TCC TCA AAG GCC CCT CCC CCC AGC CTT CCA AGC CCA TCC CGA        484
Ser Ser Ser Ser Lys Ala Pro Pro Pro Ser Leu Pro Ser Pro Ser Arg
            120                 125                 130

CTC CCG GGG CCC TCG GAC ACC CCG ATC CTC CCA CAA TAAAGGCTTC             530
Leu Pro Gly Pro Ser Asp Thr Pro Ile Leu Pro Gln
135                 140                 145

TCAATCCGC                                                              539

(2) INFORMATION FOR SEQ ID NO:2:

(i) SEQUENCE CHARACTERISTICS:
        (A) LENGTH: 165 amino acids
        (B) TYPE: amino acid
        (D) TOPOLOGY: linear (ii) MOLECULE TYPE: protein (xi) SEQUENCE DESCRIPTION: SEQ ID NO:2:

Met Glu Met Phe Gln Gly Leu Leu Leu Leu Leu Leu Ser Met Gly
-20                 -15                 -10                 -5

Gly Thr Trp Ala Ser Lys Glu Pro Leu Arg Pro Arg Cys Arg Pro Ile
                  1                   5                  10

Asn Ala Thr Leu Ala Val Glu Lys Glu Gly Cys Pro Val Cys Ile Thr
             15                  20                  25

Val Asn Thr Thr Ile Cys Ala Gly Tyr Cys Pro Thr Met Thr Arg Val
         30                  35                  40

Leu Gln Gly Val Leu Pro Ala Leu Pro Gln Val Val Cys Asn Tyr Arg
 45                  50                  55                  60

Asp Val Arg Phe Glu Ser Ile Arg Leu Pro Gly Cys Pro Arg Gly Leu
                 65                  70                  75

Asn Pro Val Ser Tyr Ala Val Ala Leu Ser Cys Gln Cys Ala Leu
             80                  85                  90

Cys Arg Arg Ser Thr Thr Asp Cys Gly Gly Pro Lys Asp His Pro Leu
         95                 100                 105

Thr Cys Asp Asp Pro Arg Phe Gln Asp Ser Ser Ser Ser Lys Ala Pro
110                 115                 120

Pro Pro Ser Leu Pro Ser Pro Ser Arg Leu Pro Gly Pro Ser Asp Thr
125                 130                 135                 140

Pro Ile Leu Pro Gln
            145

(2) INFORMATION FOR SEQ ID NO:3:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:3:

Met Thr Arg Val Leu Gln Gly Val Leu Pro Ala Leu Pro Gln
 1               5                  10
```

(2) INFORMATION FOR SEQ ID NO:4:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:4:

```
Leu Gln Gly Val Leu Pro Ala Leu Pro Gln
1               5                   10
```

(2) INFORMATION FOR SEQ ID NO:5:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:5:

```
Gly Val Leu Pro Ala Leu Pro
1               5
```

(2) INFORMATION FOR SEQ ID NO:6:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:6:

```
Leu Gln Gly Val Leu Pro Ala Leu Pro Gln Val Val Cys
1               5                   10
```

(2) INFORMATION FOR SEQ ID NO:7:

(i) SEQUENCE CHARACTERISTICS:
        (A) LENGTH: 11 amino acids
        (B) TYPE: amino acid
        (D) TOPOLOGY: both (ii) MOLECULE TYPE: peptide (xi) SEQUENCE DESCRIPTION: SEQ ID NO:7:

```
Thr Cys Asp Asp Pro Arg Phe Gln Asp Ser Ser
1               5                   10
```

(2) INFORMATION FOR SEQ ID NO:8:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO:8:

```
Met Thr Arg Val Leu Gln Gly Val Leu Pro Ala Leu Pro
1               5                   10
```

(2) INFORMATION FOR SEQ ID NO:9:

(i) SEQUENCE CHARACTERISTICS:

(A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:9:

Thr Arg Val Leu Gln Gly Val Leu Pro Ala Leu Pro
    1               5                   10

(2) INFORMATION FOR SEQ ID NO:10:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:10:

Arg Val Leu Gln Gly Val Leu Pro Ala Leu Pro
    1               5                   10

(2) INFORMATION FOR SEQ ID NO:11:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:11:

Val Leu Gln Gly Val Leu Pro Ala Leu Pro
    1               5                   10

(2) INFORMATION FOR SEQ ID NO:12:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:12:

Val Leu Gln Gly Val Leu Pro Ala Leu Pro Gln Val Val Cys
    1               5                   10

(2) INFORMATION FOR SEQ ID NO:13:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:13:

Leu Gln Gly Val Leu Pro Ala Leu Pro
    1               5

(2) INFORMATION FOR SEQ ID NO:14:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:14:

Gln Gly Val Leu Pro Ala Leu Pro
    1               5

(2) INFORMATION FOR SEQ ID NO:15:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:15:

Leu Gln Gly Val Leu Pro Ala Leu Pro Gln
    1               5                   10

(2) INFORMATION FOR SEQ ID NO:16:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:16:

Leu Gln Gly Val Leu Pro Ala Leu Pro Gln Val
    1               5                   10

(2) INFORMATION FOR SEQ ID NO:17:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:17:

Leu Gln Gly Val Leu Pro Ala Leu Pro Gln Val Val
    1               5                   10

(2) INFORMATION FOR SEQ ID NO:18:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:18:

Leu Gln Gly Val Leu Pro Ala Leu Pro Gln Val Val Cys Asn
    1               5                   10

(2) INFORMATION FOR SEQ ID NO:19:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:19:

Gly Val Leu Pro Ala Leu Pro Gln
    1               5

(2) INFORMATION FOR SEQ ID NO:20:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:20:

Gly Val Leu Pro Ala Leu Pro Gln Val
    1           5

(2) INFORMATION FOR SEQ ID NO:21:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:21:

Gly Val Leu Pro Ala Leu Pro Gln Val Val
    1           5                10

(2) INFORMATION FOR SEQ ID NO:22:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:22:

Gly Val Leu Pro Ala Leu Pro Gln Val Val Cys Asn
    1           5                10

(2) INFORMATION FOR SEQ ID NO:23:

(i) SEQUENCE CHARACTERISTICS:
        (A) LENGTH: 98 amino acids
        (B) TYPE: amino acid
        (D) TOPOLOGY: linear (ii) MOLECULE TYPE: peptide (xi) SEQUENCE DESCRIPTION: SEQ ID NO:23:

Val Leu Pro Ala Leu Pro Gln Val Val Cys Asn Tyr Arg Asp Val Arg
    1           5                10               15

Phe Glu Ser Ile Arg Leu Pro Gly Cys Pro Arg Gly Leu Asn Pro Val
                20                25               30

Val Ser Tyr Ala Val Ala Leu Ser Cys Gln Cys Ala Leu Cys Arg Arg
              35                40               45

Ser Thr Thr Asp Cys Gly Gly Pro Lys Asp His Pro Leu Thr Cys Asp
        50                55               60

Asp Pro Arg Phe Gln Asp Ser Ser Ser Lys Ala Pro Pro Ser
    65                70              75              80

Leu Pro Ser Pro Ser Arg Leu Pro Gly Pro Ser Asp Thr Pro Ile Leu
                   85                90               95

Pro Gln (2) INFORMATION FOR SEQ ID NO:24:

(i) SEQUENCE CHARACTERISTICS:
    (A) LENGTH: 88 amino acids
    (B) TYPE: amino acid
    (D) TOPOLOGY: linear (ii) MOLECULE TYPE: peptide (xi) SEQUENCE DESCRIPTION: SEQ ID NO:24:

Asn Tyr Arg Asp Val Arg Phe Glu Ser Ile Arg Leu Pro Gly Cys Pro
1               5                   10                  15

Arg Gly Leu Asn Pro Val Val Ser Tyr Ala Val Ala Leu Ser Cys Gln
            20                  25                  30

Cys Ala Leu Cys Arg Arg Ser Thr Thr Asp Cys Gly Gly Pro Lys Asp
                35                  40                  45

His Pro Leu Thr Cys Asp Asp Pro Arg Phe Gln Asp Ser Ser Ser Ser
    50                  55                  60

Lys Ala Pro Pro Ser Leu Pro Ser Pro Ser Arg Leu Pro Gly Pro
65                  70                  75                  80

Ser Asp Thr Pro Ile Leu Pro Gln
                85

(2) INFORMATION FOR SEQ ID NO:25:

(i) SEQUENCE CHARACTERISTICS:
        (A) LENGTH: 37 amino acids
        (B) TYPE: amino acid
        (D) TOPOLOGY: linear (ii) MOLECULE TYPE: peptide (xi) SEQUENCE DESCRIPTION: SEQ ID NO:25:

Thr Cys Asp Asp Pro Arg Phe Gln Asp Ser Ser Ser Ser Lys Ala Pro
1               5                   10                  15

Pro Pro Ser Leu Pro Ser Pro Ser Arg Leu Pro Gly Pro Ser Asp Thr
            20                  25                  30

Pro Ile Leu Pro Gln
        35

(2) INFORMATION FOR SEQ ID NO:26:

(i) SEQUENCE CHARACTERISTICS:
        (A) LENGTH: 14 amino acids
        (B) TYPE: amino acid
        (D) TOPOLOGY: circular (ii) MOLECULE TYPE: peptide (xi) SEQUENCE DESCRIPTION: SEQ ID NO:26:

Cys Leu Gln Gly Val Leu Pro Ala Leu Pro Gln Val Val Cys
1               5                   10